US00RE49710E

(19) United States
(12) Reissued Patent
Sun

(10) Patent Number: US RE49,710 E
(45) Date of Reissued Patent: *Oct. 24, 2023

(54) SYSTEMS, METHODS, AND DEVICES FOR STATIC AND DYNAMIC BODY MEASUREMENTS

(71) Applicant: Nextiles, Inc., Brooklyn, NY (US)

(72) Inventor: George L. Sun, Brooklyn, NY (US)

(73) Assignee: Nextiles, Inc., Brooklyn, NY (US)

( * ) Notice: This patent is subject to a terminal disclaimer.

(21) Appl. No.: 17/401,256

(22) Filed: Aug. 12, 2021

Related U.S. Patent Documents

Reissue of:
(64) Patent No.: 10,378,975
Issued: Aug. 13, 2019
Appl. No.: 16/237,314
Filed: Dec. 31, 2018

U.S. Applications:
(60) Provisional application No. 62/695,004, filed on Jul. 7, 2018, provisional application No. 62/622,845, filed on Jan. 27, 2018.

(51) Int. Cl.
*G01L 1/14* (2006.01)
*G01B 7/16* (2006.01)
(Continued)

(52) U.S. Cl.
CPC ..... *G01L 1/205* (2013.01); *A61B 5/02438* (2013.01); *A61B 5/0536* (2013.01);
(Continued)

(58) Field of Classification Search
CPC ..... G06F 3/0443; G06F 3/0414; G06F 3/045; G06F 3/0446; G06F 3/044;
(Continued)

(56) References Cited

U.S. PATENT DOCUMENTS 10,605,680 B2 * 3/2020 Sun ..... G06F 3/0443
11,255,030 B2 * 2/2022 Pilz ..... D04B 1/14
(Continued)

OTHER PUBLICATIONS

Castano, Lina M., and Alison B. Flatau. "Smart fabric sensors and e-textile technologies: A review." Smart Materials and Structures 23.5 (2014): 053001.

(Continued)

*Primary Examiner* — Elizabeth L McKane
(74) *Attorney, Agent, or Firm* — Finnegan, Henderson, Farabow, Garrett & Dunner, LLP

(57) ABSTRACT

In various aspects, embodiments of the disclosure are generally directed to measuring static and dynamic forces of a body using sensors. In particular, a sensor may include a first layer serving as a flexible support material; a second layer on the first layer, the second layer serving as a sensing material; and a third layer on the second layer, the third layer comprising an insulating material. Further, the second layer and the third layer may be coupled using a first electrode comprising a first conductive thread and a first non-conductive thread. Additionally, the first conductive thread may be embedded in the second layer. Also, the first layer and the second layer may be further coupled using a second electrode comprising a second conductive thread and a second non-conductive thread, the second conductive thread may be embedded in the second layer.

30 Claims, 26 Drawing Sheets

(51) Int. Cl.

| | |
|---|---|
| ***A61B 5/053*** | (2021.01) |
| ***G01L 1/20*** | (2006.01) |
| ***A61B 5/024*** | (2006.01) |
| ***A61B 5/0536*** | (2021.01) |
| ***A61B 5/11*** | (2006.01) |
| ***A61B 5/00*** | (2006.01) |
| *A61B 5/296* | (2021.01) |
| *A61B 5/0531* | (2021.01) |
| *A61B 5/08* | (2006.01) |
| *G06F 3/044* | (2006.01) |

(52) U.S. Cl.
CPC ..... *A61B 5/11* (2013.01); *A61B 5/6804* (2013.01); *G01B 7/16* (2013.01); *A61B 5/053* (2013.01); *A61B 5/0531* (2013.01); *A61B 5/0816* (2013.01); *A61B 5/296* (2021.01); *A61B 2562/0214* (2013.01); *A61B 2562/12* (2013.01); *G06F 3/044* (2013.01)

(58) Field of Classification Search
CPC ... G06F 2203/04102; G01B 7/16; A61B 5/11; A61B 5/02438; A61B 5/6804; A61B 5/0536; A61B 5/053; A61B 2562/0214; A61B 5/0531; A61B 5/0816; A61B 5/296; A61B 2562/12; G01L 1/205
See application file for complete search history.

(56) References Cited

U.S. PATENT DOCUMENTS

2008/0307899 A1* 12/2008 Von Lilienfeld-Toal ..... G01L 1/205 73/862.68
2016/0018274 A1* 1/2016 Seitz ..... G01D 5/2417 73/862.626
2018/0116559 A1* 5/2018 Otaka ..... A61L 31/06
2018/0340847 A1* 11/2018 Pan ..... G01L 1/146
2018/0364804 A1* 12/2018 Hoen ..... G06F 3/014

OTHER PUBLICATIONS

Zeng, Wei, et al. "Fiber-based wearable electronics: aAreview of materials, fabrication, devices, and applications." Advanced Materials 26.31 (2014): 5310-5336.
Post, Ernest Rehmatulla, et al. "E-broidery: Design and fabrication of textile-based computing." IBM Systems Journal 39.3.4 (2000): 840-860.
Wang, Yangyong, et al. "Novel fabric pressure sensors: Design, fabrication, and characterization." Smart Materials and Structures 20.6 (2011): 065015.
Gioberto, Guido, and Lucy E. Dunne. "Overlock-stitched stretch sensors: Characterization and effect of fabric property." Journal of Textile and Apparel, Technology and Management 8.3 (2013).
Shu, Lin, et al. "In-shoe plantar pressure measurement and analysis system based on fabric pressure sensing array." IEEE Transactions on Information Technology in Biomedicine 14.3 (2010): 767-775.
Meyer, Jan, et al. "Design and modeling of a textile pressure sensor for sitting posture classification." IEEE Sensors Journal 10.8 (2010): 1391-1398.
Takamatsu, Seiichi, et al. "Fabric pressure sensor array fabricated with die-coating and weaving techniques." Sensors and Actuators A: Physical 184 (2012): 57-63.
Lee, Jaehong, et al. "Conductive fiber-based ultrasensitive textile pressure sensor for wearable electronics." Advanced materials 27.15 (2015): 2433-2439.
Hasegawa, Yoshihiro, et al. "Fabrication of a wearable fabric tactile sensor produced by artificial hollow fiber." Journal of Micromechanics and Microengineering 18.8 (2008): 085014.
Jung, Sungmook, et al. "Reverse-micelle-induced porous pressure-sensitive rubber for wearable human-machine interfaces." Advanced Materials 26.28 (2014): 4825-4830.

* cited by examiner

EFFECT OF CONDUCTIVE LAYER THICKNESS ON SENSING CAPABILITIES

SYSTEMS, METHODS, AND DEVICES FOR STATIC AND DYNAMIC BODY MEASUREMENTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a non-provisional of and claims the benefit of priority to U.S. Ser. No. 62/622,845, filed on Jan. 27, 2018 and entitled "Design, fabrication, and use of wearable sensors and controllers in the shoe to monitor, analyze, and assist in gait and other bodily movements," and to U.S. Ser. No. 62/695,004, filed on Jul. 7, 2018 and entitled "Design, fabrication, and use of wearable sensors for body movement and machine learning applications," the entire disclosures of both of which are incorporated by reference in their entireties herein.

BACKGROUND OF THE INVENTION

The present discussion includes background that might be helpful to understanding the present invention, but may not constitute prior art.

Sensors represent devices that are used to collect data about the environment, and accordingly may be used in numerous everyday objects. In various aspects, sensors may be of various types including electronic devices, electromechanical devices, electro-optical devices, and the like. Moreover, advances in micromachinery and microcontroller platforms has led to the increase use of sensors in determining a variety of environmental variables including temperature, pressure, and flow.

Pressure sensitive sensors have a wide range of applications in industry, sports, and medicine primarily due to their ease of use, relatively simple construction, and direct input-to-output sensing mechanism. Current construction primarily focuses on force sensitive resistors (FSRs), where a material's resistance changes as a function of applied force. Other methods include capacitive/inductive touch, strain resistance, infrared and optical methods, to name a few. However, FSRs have become the preferred sensing modality because construction is relatively cheap, easy, and industrially accessible; however, the largest constraint for sports and health-care application is designing custom and tunable form-factors that can fit into complex geometries and shapes. More so, pressure sensitive sensors need to tolerate excessive use if designed for the human body, and more so, comfortably fit into a user's clothing or seamlessly contact the skin without causing pain, discomfort, or unnecessary disturbances.

It is against this background that the present invention was developed.

BRIEF SUMMARY OF THE INVENTION

The following presents a summary to provide a basic understanding of one or more embodiments of the disclosure. This summary is not intended to identify key or critical elements, or to delineate any scope of particular embodiments or any scope of the claims. Its sole purpose is to present concepts in a simplified form as a prelude to the more detailed description that is presented later. In one or more embodiments described herein are systems, methods, and apparatuses that describe various aspects of static and dynamic body measurements.

According to an embodiment, a device is provided. The device may include a sensor, which may further include: a first layer serving as a flexible support material; a second layer on the first layer, the second layer serving as a sensing material; and a third layer on the second layer, the third layer comprising an insulating material. Further, the second layer and the third layer may be coupled using a first electrode comprising a first conductive thread and a first non-conductive thread. Additionally, the first conductive thread may be embedded in the second layer. Also, the first layer and the second layer may be further coupled using a second electrode comprising a second conductive thread and a second non-conductive thread, the second conductive thread may be embedded in the second layer.

According to one or more example embodiments, a method is provided. The method may be used for fabricating a sensor. The method may include: providing a first layer serving as a flexible support material; disposing a second layer on the first layer, the second layer serving as a sensing material; disposing a third layer on the second layer, the third layer comprising an insulating material; coupling the second layer and the third layer using a first electrode comprising a first conductive thread and a first non-conductive thread, the first conductive thread embedded in the second layer; and coupling the first layer and the second layer using a second electrode comprising a second conductive thread and a second non-conductive thread, the second conductive thread embedded in the second layer.

BRIEF DESCRIPTION OF THE DRAWINGS

The accompanying figures illustrate a number of exemplary embodiments and are a part of the specification. Together with the following description, these figures demonstrate and explain various principles of the instant disclosure.

Figure 1A:
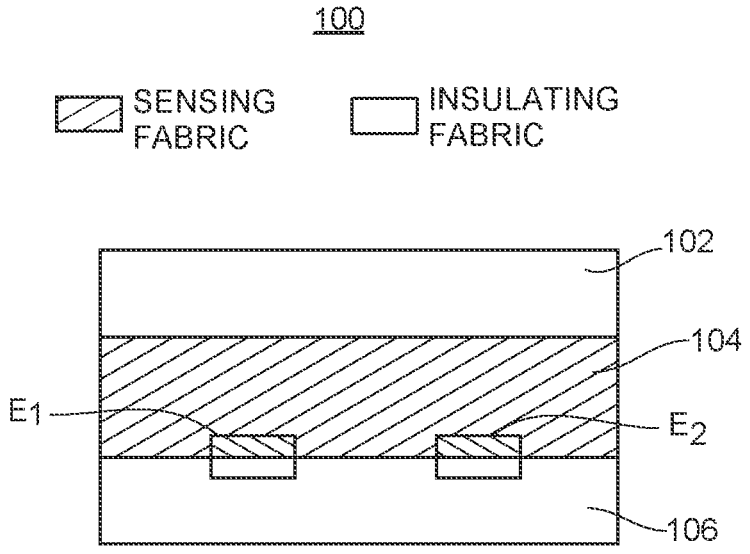
FIG. 1A shows a diagram of a cross-sectional view of an example sensor in a sensing architecture, in accordance with example embodiments of the disclosure.

Throughout the figures, identical reference characters and descriptions indicate similar, but not necessarily identical, elements. While the exemplary embodiments described herein are susceptible to various modifications and alternative forms, specific embodiments have been shown by way of example and will be described in detail herein. However, the exemplary embodiments described herein are not intended to be limited to the particular forms disclosed. Rather, the instant disclosure covers all modifications, equivalents, and alternatives falling within this disclosure.

DETAILED DESCRIPTION OF THE INVENTION

As will be explained in greater detail below, embodiments of the instant disclosure are generally directed to providing static and dynamic body measurements, and methods and systems for manufacturing apparatuses for the same.

In various aspects, sensors (e.g., pressure sensitive sensors) may have a wide range of applications in a variety of fields including industry, sports, medicine, and others in part due to their ease of use, relatively simple construction, and their direct input-to-output sensing mechanism. In some aspects, construction of pressure sensitive sensors may include the fabrication of force sensitive resistors (FSRs), in which a material's resistance can change as a function of an applied force. Other methods may be used, including, but not limited to, capacitive and/or inductive touch techniques, strain resistance-based techniques, infrared and/or optical methods, combinations thereof, and/or the like.

In one embodiment, FSRs may be used as a sensing modality based at least in part on because FSR construction may be relatively cheap, easy, and industrially accessible in comparison with the other techniques listed above. One constraint on FSRs that may limit potential applications (e.g., applications in sports and health-care) may be in designing custom and tunable form-factors that can fit into complex geometries and shapes. Further, pressure sensitive sensors may need to include materials capable of tolerating stress and strain resulting from excessive use (e.g., in applications geared towards the human body) without inducing material fatigue and/or breakdown. In another aspect, the pressure sensitive sensors may need to comfortably fit into a user's clothing, or may need to seamlessly contact the skin without causing pain, discomfort, or unnecessary disturbances over time.

Disclosed herein are systems, methods, and apparatuses that are directed to flexible pressure sensors including pressure sensitive materials that may be used in many applications such as in wearable devices and articles of clothing. While some of the disclosed embodiments are directed towards specific areas of the body (e.g., the foot), it is to be understood that the various disclosed embodiments may be applied for many other areas of the body including, but not limited to, shirts, pants, undergarments, hats, combinations thereof, and/or the like.

In various embodiments, embodiments of the disclosure are directed to electronic devices including such pressure sensitive sensors that include conductive and electrically sensitive materials. In another embodiment, the electronic devices may have an orthogonal sensing capability which may be imparted by the configuration of the sensors as will be further described herein. In particular, orthogonal sensing may refer to the electronic device being capable of performing independent measurements that do not influence one another, for example, pressure measurements, bend measurements, and stretch measurements. In another embodiment, the electronic device may be capable of combining multiple sensors to generate multiple signals corresponding, for example, that may correspond with a given area and/or portion of a user's body. In one embodiment, various artificial intelligence (AI)-based algorithms and/or machine learning algorithms may be implemented in connection with the disclosed electronic devices, for example, for sensing and detecting movement, position, performing predictive analytics, and/or the like. In another embodiment, various position reconstruction algorithms may be used in connection with the disclosure, including, but not limited to, EFT (Electric Field Tomography), EIT (Electric Impedance Tomography), RFDT (Radio Frequency Distance Tomography), to be described below. Such algorithms may be used, for example, to learn of a user's motion behavior over time and space.

In various embodiments, embodiments of the disclosure may find applications in many fields, including in healthcare related applications. For example, embodiments of the disclosure may be used to detect and provide feedback on a user's posture and/or gait. Further, the posture and/or gait of the user may be tracked using the sensors in combination with at least one processor and non-transitory computer-readable medium, and the tracked data may be used to determine and log improvements. In various aspects, embodiments of the disclosure may be used for injury and/or disease detection (e.g., by analysis of gait or posture data, or the like), and feedback may be provided to the user to accelerate healing and prevent further complications. In particular, various neuromuscular and/or skeletal diseases and disorders may have particular gait signatures that may be collected using the sensors embedded in footwear of users, and the data may be interpreted by one or more experts (e.g., doctors and related medical professionals) in combination with AI-based algorithms.

In various embodiments, the electronic devices disclosed herein may be incorporated with other sensors, including, but not limited to, inertial measurement units (IMUs). Non-limiting examples of such IMU components include accelerometers, gyrometers, magnetometers, barometers, and/or the like. Alternatively, or additionally, the electronic devices may be integrated with a variety of different sensors including, but not limited to, Hall effect sensors (e.g., to perform magnetic measurements), strain gauge sensors, force sensing resistors, temperature sensors, light-emitting diodes (LEDs), photodiodes, combinations thereof, and/or the like. Such sensors may provide additional data that may be combined with the data provided by the sensors described herein. The additional data may be fused with the data collected by the sensors, for example, in near-real time using a Kalman filter (or other suitable filter and/or algorithm), and dynamic actions may be taken as a result of the combined inputs (e.g., a notification may be sent to a medical professional when an accelerometer indicates a fall and a pressure sensitive sensor as described herein indicates a high force impact to a portion of the users body such as a hip or a sensitive joint).

As noted, embodiments of the disclosure as relate to the electronic devices and sensors may find many applications in a variety of industries. For example, the electronic device and sensors may find application in ergonomics. In particular, the electronic device and one or more sensors may be used to monitor one or more of the following conditions in users: (i) back bending resulting from user slouching, (ii) over-extension of back or rotation of the torso, curvature and bend of the neck, (iii) angle of hip from horizontal and knee from vertical with bend measurements, (iv) left/right twist of torso relative to hip.

Another example application of the various embodiments of the disclosure includes applications used in connection with kinetic take (e.g., kinesio tape). For example, electronic device including fabric-based sensors can be interlaced, bonded, or fabricated with kinesio tape. Moreover, the sensors may be used to determine the effectiveness of the kinesio tape. For example, the sensors may be used to measure whether the kinesio tape is limiting the amount of bending or stretching on a certain joint or muscle group of a user. In another embodiment, one or more AI-based algorithms and/or machine learning algorithms may be used in connection with the sensors and/or kinesio tape to recommend more effective areas to allocate the tape on the body of the user. Further, the algorithms may recommend if replacing the tape is necessary, or fitting a different size is necessary or recommended.

Other non-limiting example applications of the various embodiments of the disclosure include application used in connection with sports and coaching, physical therapy, augmented and/or virtual reality (e.g., the generation of motion data which can be used to generate one-to-one avatar movement). In the above applications (and similar applications), the electronic devices may be used to provide feedback to the user and/or user devices. For example, the electronic devices may be used to detect abnormal user motion and may emit a corresponding notification (e.g., phone alert, phone ring, watch alert, watch ring, buzzer, LED signal or light notifications, haptics, for example, through buzzers or ringers embedded into the electronic device).

In various embodiments, the electronic devices may have a multi-layer construction. For example, in an embodiment, the electronic device may include pressure sensitive materials and be composed of at least three components: (1) an anode that may serve to generate a signal, (2) a pressure sensitive material layer, and (3) a cathode that may serve as a reference layer, and which may be electronically grounded. In another embodiment, the electronic device may include one or more additional optional layers. For example, the electronic device may include a separator layer between the anode and cathode, for example, to prevent signal shorts. Finally, the electronic device may comprise a pressure sensitive material (e.g., a composite) that may include a fabric or soft-material layer to serve as a comfortable contact with human skin. Additional layers may be contemplated and may have additional advantages in terms of a device's input or output dynamic range, sensitivity, noise tolerance, combinations thereof, and/or the like. In various embodiments, the layers may be merged with conductive or insulating adhesive depending on the contacting interface.

In various embodiments, the electronic devices may have a single-layer construction. In another embodiment, the electronic device including the pressure sensitive material layer that may further comprise two conducting layers that may be separated laterally, rather than vertically. Accordingly, the reference layer for a multi-touch pressure sensitive material is combined to a single trace that contours around the signal layer. These traces can be cut, milled, sewn, or printed in a single layer and embedded onto the desired substrate. The pressure sensitive material can be placed on top of this layer and finally the entire composite can be covered in a shrouding fabric layer. In this construction, there is no need for a separator, as the positive and negative conductive layers are separated spatially on the same plane.

FIG. 1A shows a diagram of a cross-sectional view of an example sensor in a sensing architecture, in accordance with example embodiments of the disclosure. In particular, FIG. 1A shows a diagram of a sensor 100. In various embodiments, the sensor 100 may be part of a device (not shown) that may be embedded or otherwise coupled to an article of clothing. In one embodiment, the sensor 100 may include a first layer 102 serving as a flexible support material that may be an insulating material such as a fabric. In another embodiment, the sensor 100 may include a second layer 104 on the first layer 102, the second layer serving as a sensing material such as a sensing fabric, which may include a conductive material. Further, in one embodiment, the sensor 100 may include a third layer 106 on the second layer 104, the third layer 106 including an insulating material such as an insulating fabric. Moreover, the second layer 104 and the third layer 106 may be coupled (e.g., electronically and/or mechanically coupled) using a first electrode E1 comprising a first conductive thread and a first non-conductive thread (to be described in connection with FIG. 1D, below), the first conductive thread embedded in the second layer 104. Additionally, the second layer 104 and the third layer 106 may be further coupled using a second electrode E2 comprising a second conductive thread and a second non-conductive thread, the second conductive thread embedded in the second layer. In various embodiments, a cross-sectional shape of the electrodes and/or the spacing between the electrodes may be configured to increase a response time, an input dynamic range, output dynamic range, and/or a sensitivity of the sensor. In another embodiment, a thickness of the second layer 104 including the sensing material may be between about 100 microns to several centimeters, and the thickness of the sensing material may be configured to increase a response time, an input dynamic range, output dynamic range, and/or a sensitivity of the sensor 100. In another embodiment, the sensing material may be fabricated using an electrospinning and/or spraying technique, in which case the thickness of the sensing material may be between approximately 100 nm to approximately 1 mm.

In various embodiments, although one sensor (e.g., sensor 100) was described in connection with FIG. 1A, various embodiments may be contemplated where multiple sensors (e.g., 1, 2, 10, 100, 1000 . . . N sensors, where N is an integer) may be positioned within a fixed distance (e.g., tolerance) of each other on a horizontal plane corresponding to the in-plane axis of a portion of an article of clothing such as a garment or an insole of a shoe. In particular, as many sensors as desired may be added in such a horizontal place as long as the sensors are able to fit (e.g., the inter-sensor spacing may be configured to allow for the maximum packing of sensors such that the electrodes and various conductive traces of each sensor do not physically and/or electronically overlap). In another embodiment, the sensor spacing may be determined based on an electromagnetic interference (EMI) test of the sensors. In particular, the spacing may be determined such that the sensors do not generate electromagnetic cross-coupling beyond a given threshold, as such EMI may lead to coupled sensor output. Moreover, in some embodiments, the multiple sensors on a given horizontal plane may include a common electrode that may be shared between at least a subset of the sensors.

Figure 1B:
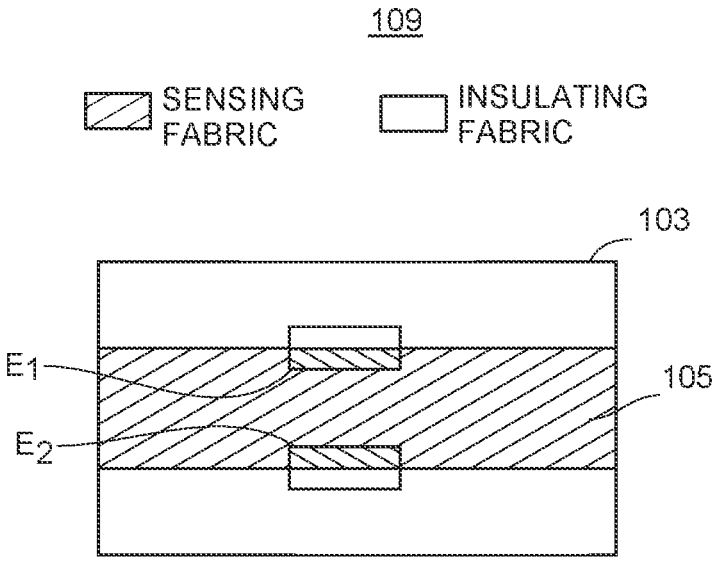
FIG. 1B shows a diagram of another cross-sectional view of an example sensor, in accordance with example embodiments of the disclosure.

FIG. 1B shows a diagram of another cross-sectional view of an example sensor, in accordance with example embodiments of the disclosure. In particular, FIG. 1B shows another diagram of a sensor 109. In particular, FIG. 1B shows a diagram of a sensor 109 having a different configuration (e.g., vertical configuration of electrodes E1 and E2) with respect to FIG. 1A. In various embodiments, the sensor 109 may also be part of a device (not shown) that may be embedded or otherwise coupled to an article of clothing. In particular, the sensor 109 may work in conjunction with sensor 100 as part of the same device or as part of a different device that may be embedded or otherwise coupled to an article of clothing.

In one embodiment, the sensor 109 may again include a first layer 103 serving as a flexible support material that may be an insulating material such as a fabric. In another embodiment, the sensor 109 may also include a second layer 105 on the first layer 103, the second layer serving as a sensing material such as a sensing fabric, which may include a conductive material. Further, in one embodiment, the sensor 109 may include a third layer 107 on the second layer 105, the third layer 107 including an insulating material such as an insulating fabric. Moreover, the first layer 103 and the second layer 105 may be coupled (e.g., electronically and/or mechanically coupled) using a first electrode E1 comprising a first conductive thread and a first non-conductive thread (to be described in connection with FIG. 1D, below), the first conductive thread embedded in the second layer 105. Additionally, the second layer 105 and the third layer 107 may be further coupled using a second electrode E2 comprising a second conductive thread and a second non-conductive thread, the second conductive thread embedded in the second layer 105. In various embodiments, a cross-sectional shape of the electrodes and/or the spacing between the electrodes may be configured to increase a response time, an input dynamic range, output dynamic range, and/or a sensitivity of the sensor. In another embodiment, a thickness of the second layer 105 including the sensing material may be between about 100 microns to several centimeters, and the thickness of the sensing material may be configured to increase a response time, an input dynamic range, output dynamic range, and/or a sensitivity of the sensor. In another embodiment, the sensing material may be fabricated using an electrospinning and/or spraying technique, in which case the thickness of the sensing material may be between approximately 100 nm to approximately 1 mm.

In various embodiments, similar to the discussion for FIG. 1A, although one sensor (e.g., sensor 109) is described in connection with FIG. 1B, various embodiments may be contemplated where multiple sensors (e.g., 1, 2, 10, 100, 1000 . . . N sensors, where N is an integer) may be positioned within a fixed distance (e.g., tolerance) of each other on a horizontal plane corresponding to the in-plane axis of a portion of an article of clothing such as a garment or an insole of a shoe.

Figure 11A:
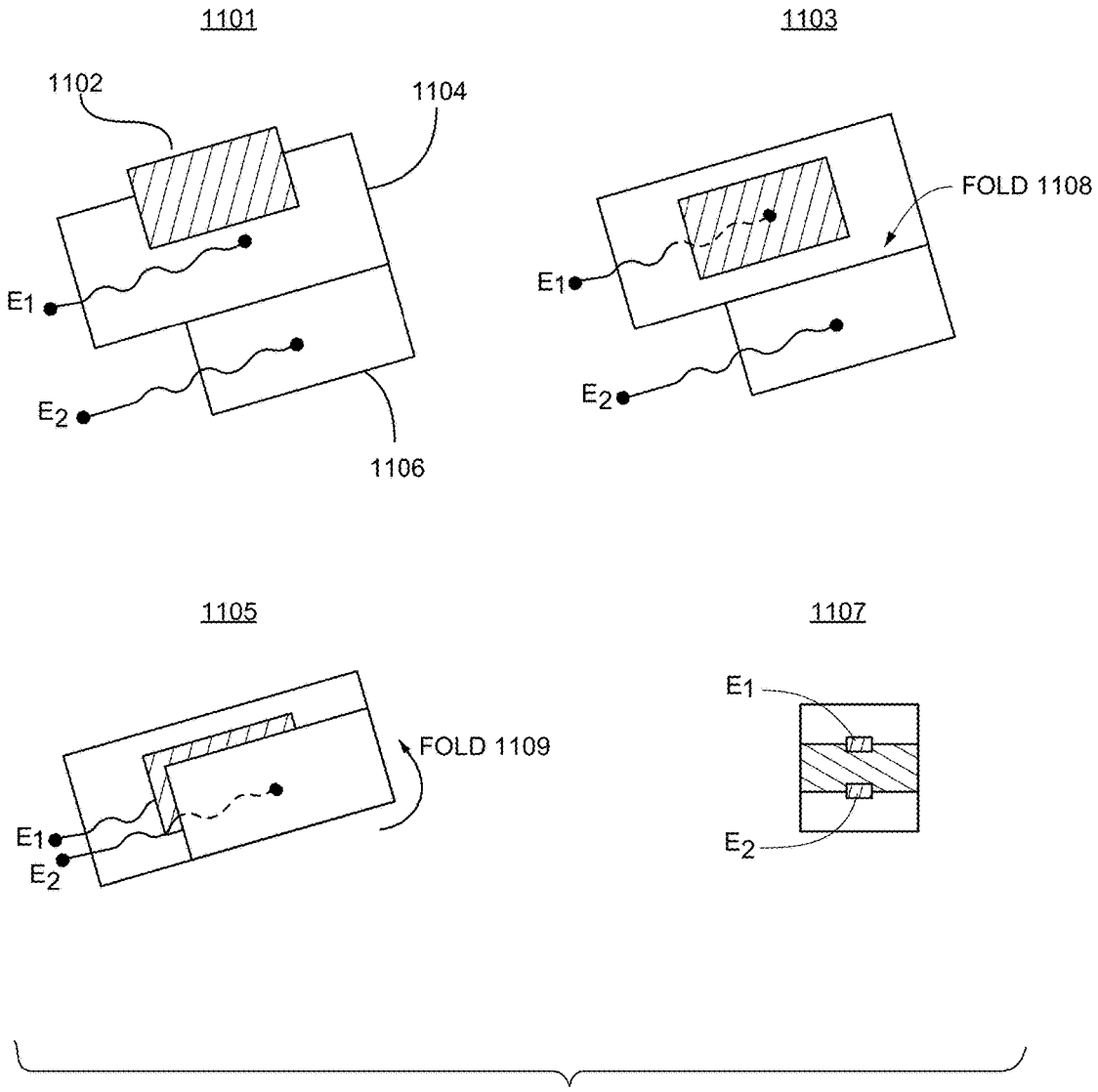
FIG. 11A-11C show diagrams that describe various aspects of the coupling of a sensing material and a portion of an article of clothing, in accordance with example embodiments of the disclosure.

In various embodiments, the sensors 100 and 109 depicted in FIGS. 1A and 1B may be stacked vertically or horizontally, or both. Further, the sensors may be fabricated individually and stacked vertically or positioned horizontally or both, after fabrication. In various embodiments, vertically stacked sensors may be secured to one another and/or an article of clothing such as a portion of a garment using non-conductive threads. In another embodiment, multiple sensors can be fabricated on a given horizontal plane of at least a portion of an article of clothing such as a garment; further, the sensors and/or the portion of the article of clothing may be spatially configured (e.g., folded together)

in order to position the sensors in stacked vertical configuration, as will be further shown and described herein in connection with FIG. 11A.

In various embodiments, stacking sensors may yield several advantages, including, but not limited to, one or more of the following. In an aspect, such a configuration of sensors may increase the signal-to-noise ratio (SNR) of an electronic device having the stacked sensors. In particular, the signal from the stacked sensors can be averaged to reduce noise. In another aspect, devices including stacked sensors may not have any appreciable reduction in the response time, input dynamic range, output dynamic range, and/or device sensitivity (see FIGS. 11, and 13-16 and related discussion for more description related to these parameters); this may be based at least in part on the fact that the sensors may operate independently from one another (e.g., the sensor configuration may impart an orthogonal sensing capability). In another aspect, the number of wires and connections to a given electronic device (e.g., at the electronic device's electrodes) having multiple sensors may be increased, while the device may be configured to output one (averaged) value for a given measurement (e.g., a force, a pressure, and the like). In another aspect, the stacked sensors may be used to generate depth sensing data. For example, a first sensor in the stack of sensors that is closest to a portion of the user's body undergoing movement may generate a measurement with relatively little force input, while more force is required to activate the deepest sensor in the stack of sensors. Accordingly, a gradient of signals representing force measurements may be generated down the vertical stack of sensors which may be used to determine the amount of force that penetrated into a given portion of an article of clothing and at what distance that force penetrated into the article of clothing. In another embodiment, a device configured to have the multiple sensors may become thicker and/or bulky; accordingly, the form-factor and comfort of the user wearing an article of clothing including the device may need to be weighed against the advantages described above.

Figure 1C:
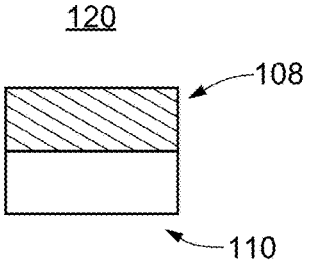
FIG. 1C shows a diagram of a cross-sectional view of an example electrode that can be used in connection with a sensor, in accordance with example embodiments of the disclosure.

FIG. 1C shows a diagram of a cross-sectional view of an example electrode that can be used in connection with a sensor, in accordance with example embodiments of the disclosure. In particular, the electrode 120 may include a first portion 108, the first portion including at least some of the sensing material (e.g., sensing fabric). Moreover, the electrode 120 may include a second portion 110 including at least some of the insulating material (e.g., insulating fabric). Moreover, the electrodes may be threaded in order to couple to the first portion 108 and the second portion 110 of the electrode 120 as shown and described in connection with FIG. 1D, below. Further, in an embodiment, conductive thread may be embedded in the first portion 108 including the sensing material, while non-conductive thread may be embedded in the second portion 110 including the insulating material.

In some embodiments, the various layers (e.g., the layers serving as a flexible support material, sensing materials, and/or insulating materials) may have a material composition that includes a fabric and/or a polymer. In various embodiments, the fabrics may include, but not be limited to, one or more of the following materials: organza, denim, velvet, brocade, corduroy, flannel, crepe, damask, felt, tweed, gauze, lawn cloth, charmeuse, khaki, tartan, combinations thereof, and/or the like. In another embodiment, the sensing material and/or any insulating or support materials may include flexible materials including, but not be limited to, one or more of mylar, epoxy, polyethylene terephthalate (PET), polyethylene (PE), polypropylene (PP), polystyrene (PS), polyvinyl chloride (PVC), polyamide (PA), combinations thereof, and/or the like.

In various embodiments, the various layers shown in FIGS. 1A and 1B (e.g., second layers 104 and 105) including the sensing materials may include a dopant. Further, the dopant may include any suitable concentration of a material including compounds having materials from at least groups I, II, III, IV, V, VI, VII, or transition metals of the periodic table of elements. In various embodiments, the dopants may include group I elements including, but not limited to, lithium, sodium, and/or the like. The dopants may further include group II elements including, but not limited to, magnesium, calcium, and/or the like. The dopants may further include group III elements including, but not limited to, boron, aluminum, gallium, and/or the like. The dopants may further include group IV elements including, but not limited to, silicon, germanium, and/or the like. The dopants may further include group V elements including, but not limited to, phosphorus, arsenic, and/or the like. The dopants may further include group VI elements including, but not limited to, sulfur, selenium, and/or the like. The dopants may further include group VII elements including, but not limited to, chlorine, bromine, and/or the like. Further, the dopants may further include transition metals including, but not limited to, nickel, zinc, and/or the like. The dopants may further include, but not be limited to, rare-earth metals, such as the lanthanide series. More complex dopants may include combinations of at least the dopants listed above, for example, cadmium sulfide. Examples of such complex dopants may include, but not be limited to, gallium arsenide, gallium phosphide, gallium nitride, cadmium telluride, cadmium sulfide, and combinations thereof.

In some embodiments, the electrodes described herein and depicted for example, in FIG. 1C (e.g., electrode 120) may be structured in a number of different ways. For example, cross-section or an overhead section of an electrode may form a non-angular shape, or may be a more complex shape (e.g., patterned or freeform). In some embodiments, the electrode may be shaped to allow compression and expansion of the electroactive device during operation (e.g., under the application of pressure by various part of the body).

In some embodiments, an electrode (e.g., electrode 120) may include metals such as aluminum, gold, silver, tin, copper, indium, gallium, zinc, and the like. Other conductive materials may be used, including carbon nanotubes, graphene, transparent conductive oxides (TCOs, e.g., indium tin oxide (ITO), zinc oxide (ZnO), etc.), and the like.

In some configurations, it may be necessary for the electrodes (e.g., electrodes E1 and E2 of FIGS. 1A and 1B) to stretch elastically. In such embodiments, the electrodes may include TCOs, graphene, carbon nanotubes, and the like. In other embodiments, for example, embodiments, relatively rigid electrodes (e.g. electrodes including a metal such as aluminum) may be used. In some embodiments, the electrodes may have a thickness of approximately 100 nm to approximately 10 mm, with an example thickness of approximately 10 microns to approximately 1 mm. In some embodiments, the electrodes may be fabricated using any suitable process. For example, the electrodes may be fabricated using physical vapor deposition (PVD), chemical vapor deposition (CVD), sputtering, spray-coating, spin-coating, atomic layer deposition (ALD), and the like. In another aspect, the electrodes may be manufactured using a thermal evaporator, a sputtering system, a spray coater, a spin-coater, an ALD unit, combinations thereof, and/or the like.

Figure 1D:
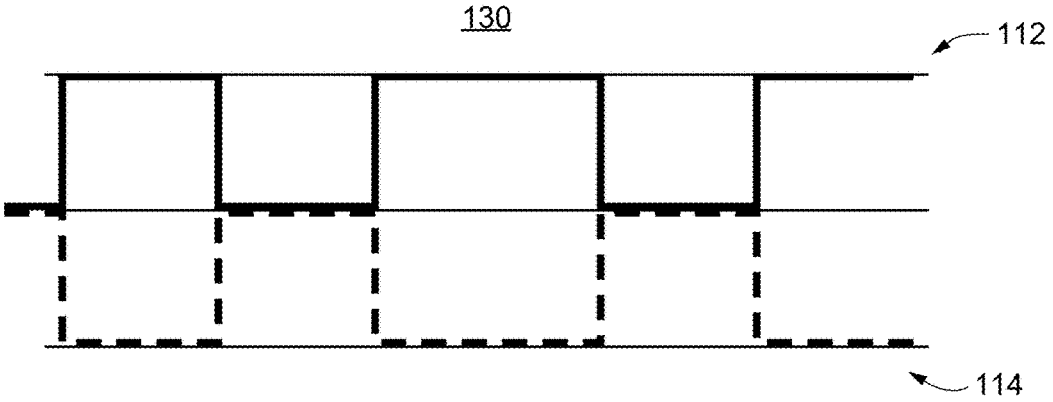
FIG. 1D shows a diagram of a cross-sectional view of an example threading scheme that can be used in connection with a sensor, in accordance with example embodiments of the disclosure.

FIG. 1D shows a diagram of a cross-sectional view of an example threading scheme that can be used in connection with a sensor, in accordance with example embodiments of the disclosure. In particular, diagram 130 shows a first thread 112 and a second thread 114 that may be used to stitch together a portion of a sensing material (e.g., layer 104 or 105 of FIGS. 1A and 1B, respectively) to a portion of an insulating material (e.g., layer 106 or layers 103 and 107 of FIGS. 1A and 1B, respectively). Further, the first thread 112 may include a conductive material, while the second thread 114 may include a non-conductive material.

In some embodiments, the conductive thread may include any suitable metal, semiconductor material, or conductive polymer. Non-limiting examples may include, but not be limited to, organic conductive materials such as poly(3,4-ethylenedioxythiophene) polystyrene sulfonate (PEDOT-PSS), PEDOT-PSS and polyvinyl alcohol (PVA), polypyrrole (PPy), polyaniline (PANI), combinations thereof, and/or the like. In some embodiments, the materials used to make a conductive thread can also be used as a dopant. For example, a nickel conductive thread can be doped with trace amounts of copper and vice-versa. As noted, the dopants may additional include group I elements including, but not limited to, lithium, sodium, and/or the like. The dopants may further include group II elements including, but not limited to, magnesium, calcium, and/or the like. The dopants may further include group III elements including, but not limited to, boron, aluminum, gallium, and/or the like. The dopants may further include group IV elements including, but not limited to, silicon, germanium, and/or the like. The dopants may further include group V elements including, but not limited to, phosphorus, arsenic, and/or the like. The dopants may further include group VI elements including, but not limited to, sulfur, selenium, and/or the like. The dopants may further include group VII elements including, but not limited to, chlorine, bromine, and/or the like. Further, the dopants may further include transition metals including, but not limited to, nickel, zinc, and/or the like. The dopants may further include, but not be limited to, rare-earth metals, such as the lanthanide series. More complex dopants may include combinations of at least the dopants listed above, for example, gallium arsenide, gallium phosphide, gallium nitride, cadmium telluride, cadmium sulfide, and combinations thereof.

In various embodiments, the conductive thread 112 and/or the non-conductive thread 114 may be sown using a sewing or embroidery machine. In particular, the conductive thread either may be configured on the bobbin or sewing needle and can be sewn on the bottom or top of a fabric by adjusting the tension on the sewing needle. In another embodiment, a higher tension on the needle may pull the bobbin and sewing thread to the top of the sewn material, that is, for example, to the sensing material. In another embodiment, a looser tension may serve to pull the bobbin and sewing thread to the bottom of the sewn material, for example, to the insulating material. Accordingly, an average tension on the sewing need may serve to keep a bobbin thread on the bottom, while the sewing thread on the top as shown in FIG. 1D.

In some embodiments, as will be further described in connection with the various diagrams of FIG. 13-16, a density per unit area of a stitching of the conductive threads associated with the electrodes may be configured to increase a response time, an input dynamic range, an output dynamic range, and/or a sensitivity of the sensors. In another embodiment, the radius of the conductive threads may be configured to increase one or more of a response time, an input dynamic range, output dynamic range, or a sensitivity of the sensor.

Figure 2A:
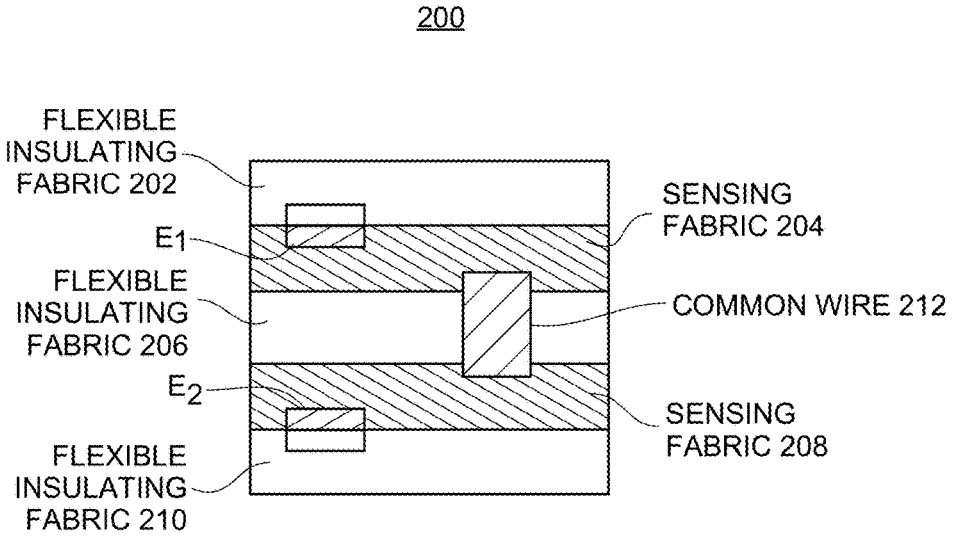
FIG. 2A shows a diagram of a cross-sectional view of an example sensor in another sensing architecture, in accordance with example embodiments of the disclosure.

FIG. 2A shows a diagram of a cross-sectional view of an example sensor in another sensing architecture, in accordance with example embodiments of the disclosure. In particular, FIG. 2A shows a diagram of a cross-sectional view of an example sensor having a vertical architecture of sensing materials, in accordance with example embodiments of the disclosure.

In various embodiments, the sensor 200 may be part of a device (not shown) that may be embedded or otherwise coupled to an article of clothing. In one embodiment, the sensor 200 may include a first layer 202 serving as a flexible support material that may be an insulating material such as a fabric. In another embodiment, the sensor 200 may include a second layer 204 on the first layer 202, the second layer serving as a sensing material such as a sensing fabric, which may include a conductive material. Further, in one embodiment, the sensor 200 may include a third layer 206 on the second layer 204, the third layer 206 including an insulating material such as an insulating fabric. Moreover, the first layer 202 and the second layer 204 may be coupled (e.g., electronically and/or mechanically coupled) using a first electrode E1 comprising a first conductive thread and a first non-conductive thread (as described in connection with FIG. 1D), the first conductive thread embedded in the second layer 204.

In another embodiment, the sensor 200 may include a fourth layer 208 on the third layer 206, the second fourth serving as a sensing material such as a sensing fabric, which may include a conductive material. Further, in one embodiment, the sensor 200 may include a fifth layer 210 on the fourth layer 208, the fifth layer 210 including an insulating material such as an insulating fabric. Moreover, the fourth layer 208 and the fifth layer 210 may be coupled (e.g., electronically and/or mechanically coupled) using a second electrode E2 comprising a first conductive thread and a first non-conductive thread (as described in connection with FIG. 1D), the first conductive thread embedded in the fourth layer 208. Additionally, the sensor 200 may include a common connection 212 (also referred to as a common wire herein) that may serve to electrically couple the second layer 204 and the fourth layer 208 together, that is, the two sensing materials together.

In various embodiments, a cross-sectional shape of the electrodes and/or the spacing between the electrodes may be configured to increase a response time, an input dynamic range, output dynamic range, and/or a sensitivity of the sensor. In another embodiment, a thickness of the second layer 104 including the sensing material may be between about 100 microns to several centimeters, and the thickness of the sensing material may be configured to increase a response time, an input dynamic range, output dynamic range, and/or a sensitivity of the sensor 200. In another embodiment, the sensing material may be fabricated using an electrospinning and/or spraying technique, in which case the thickness of the sensing material may be between approximately 100 nm to approximately 1 mm.

In various embodiments, although one sensor (e.g., sensor 200) was described in connection with FIG. 2A, various embodiments may be contemplated where multiple sensors (e.g., 1, 2, 10, 100, 1000 . . . N sensors, where N is an integer) may be positioned within a fixed distance (e.g., tolerance) of each other on a horizontal plane corresponding to the in-plane axis of a portion of an article of clothing such as a garment or an insole of a shoe. In particular, as many sensors as desired may be added in such a horizontal place as long as the sensors are able to fit (e.g., the inter-sensor spacing may be configured to allow for the maximum packing of sensors such that the electrodes and various conductive traces of each sensor do not physically and/or electronically overlap). In another embodiment, the sensor spacing may be determined based on an electromagnetic interference (EMI) test of the sensors. In particular, the spacing may be determined such that the sensors do not generate electromagnetic cross-coupling beyond a given threshold, as such EMI may lead to coupled sensor output. Moreover, in some embodiments, the multiple sensors on a given horizontal plane may include a common electrode that may be shared between at least a subset of the sensors.

Figure 2B:
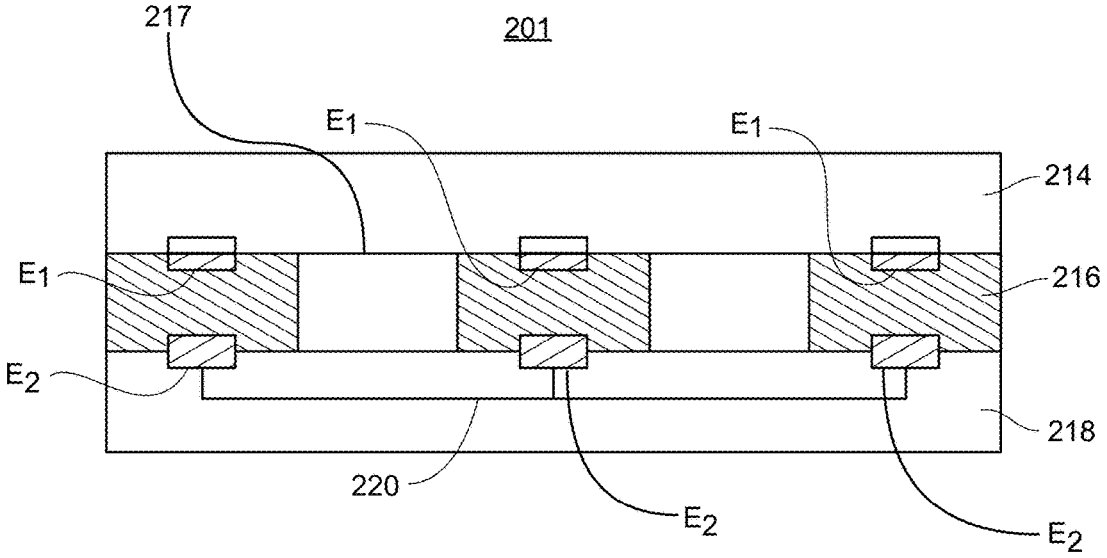
FIG. 2B shows a diagram of another cross-sectional view of an example sensor in another sensing architecture, in accordance with example embodiments of the disclosure.

FIG. 2B shows a diagram of another cross-sectional view of an example sensor in another sensing architecture, in accordance with example embodiments of the disclosure. In particular, FIG. 2B shows a diagram of a cross-sectional view of an example sensor having a horizontal architecture of sensing materials, in accordance with example embodiments of the disclosure.

In various embodiments, the sensor 201 may be part of a device (not shown) that may be embedded or otherwise coupled to an article of clothing. In one embodiment, the sensor 201 may include a first layer 214 serving as a flexible support material that may be an insulating material such as a fabric. In another embodiment, the sensor 201 may include several second layers 216 on the first layer 214, the second layers serving as a sensing material such as a sensing fabric, which may include a conductive material. Moreover, the sensor 201 may include additional second layers 217 on the first layer 214, the additional second layers serving as an insulating material between the sensing second layers 216. Further, in one embodiment, the sensor 201 may include a third layer 218 on the second layers 216 and layers 217, the third layer 218 including an insulating material such as an insulating fabric. Moreover, the first layer 214 and the second layers 216 may be coupled (e.g., electronically and/or mechanically coupled) using first electrodes E1 comprising a first conductive thread and a first non-conductive thread (as described in connection with FIG. 1D), the first conductive thread embedded in the second layers 216. Additionally, the second layers 216 and the third layer 218 may be coupled (e.g., electronically and/or mechanically coupled) using common electrodes E2 comprising a first conductive thread and a first non-conductive thread (as described in connection with FIG. 1D), the first conductive thread embedded in both second layers 216 and third layer 218. Moreover, the common electrodes E2 may be connected electronically using a common connection 220 (e.g., wired connection).

Figure 3A:
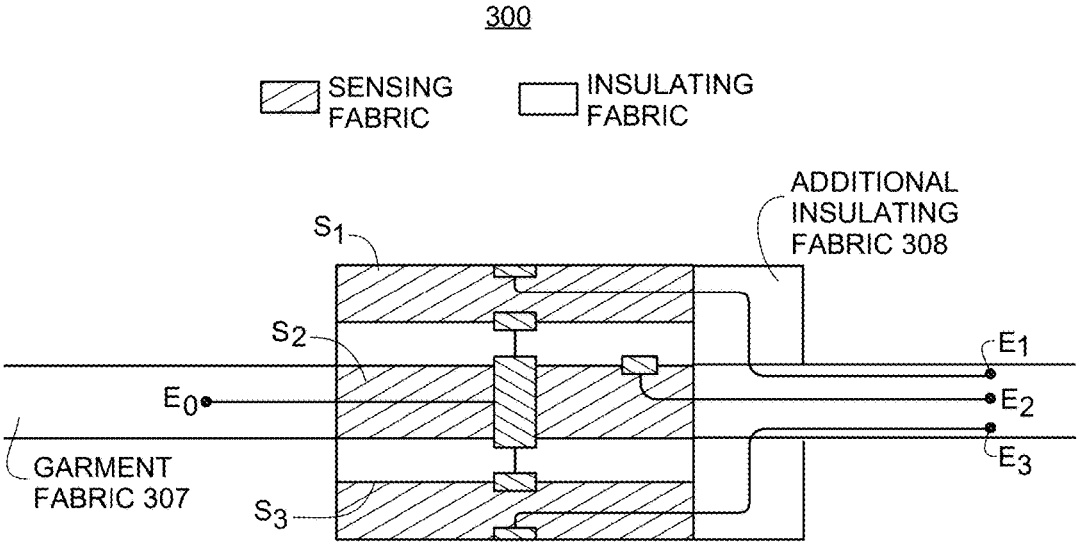
FIG. 3A shows a diagram of a cross-sectional view of an example sensor in another sensing architecture, in accordance with example embodiments of the disclosure.

FIG. 3A shows a diagram of a cross-sectional view of an example electronic device in another sensing architecture, in accordance with example embodiments of the disclosure. At least a portion of the electronic device may be disposed onto and within a garment such as garment 307. In particular, the electronic device 300 may include a first sensor S1 having a first sensing material and a first electrode E1 along a top edge of the first sensing material, the first sensing material wired to a first signal output, and a second electrode along a bottom edge of the first sensing material, the second electrode coupled to a first insulating material. Further, the electronic device may include a second sensor S2 spaced vertically from the first sensor across the first insulating material. The second sensor may include: a second sensing material and a third electrode electrically connected to the second electrode, the second sensing material wired to a common electrical connection E0, the third electrode passing from a top edge of the second sensing material to a bottom edge of the second sensing material, the third electrode coupled to a second insulating material, and a fourth electrode E2 along a top edge of the second sensing material, the fourth electrode wired to a second signal output. In some embodiments, the second sensor may need to be on a neutral axis of the device, that is, an axis that does not compress or tense when being bent, but only stretches.

In various aspects, the neutral axis may shift depending on the materials used, the thickness of the top and bottom material layers, and/or the density/weight on each side of the layers. Further, the neutral axis may not necessarily strictly mean the middle; the neutral axis may be skewed more on the top or bottom depending on the device fabrication and configuration during operation.

In another embodiment, the electronic device may include a third sensor S3 spaced vertically from the second sensor across the second insulating material. In one embodiment, the third sensor may include: a third sensing material, a fifth electrode along a top edge of the third sensing material wired to a common electrical connection E0, and a sixth electrode E3 along the bottom edge of the third sensing material. the sixth electrode wired to a third signal output.

In various embodiments, a density per unit area of a stitching of at least one of the first conductive thread, the second conductive thread, the third conductive thread, and the fourth conductive thread is configured to increase a response time, an input dynamic range, and/or a sensitivity of the sensor.

In another embodiment, a radius of at least one of the first conductive thread, the second conductive thread, the third conductive thread, and the fourth conductive thread is configured to increase one or more of a response time, an input dynamic range, or a sensitivity of the sensor. In one embodiment, the first insulating material is disposed on a top side of the article, and wherein the second insulating material is disposed on a bottom side of the article. In various embodiments, a material composition of at least of the first sensing material, the second sensing material, the third sensing material, the first insulating material, and the second insulating material is selected from the group consisting of a fabric and a polymer material. Moreover, at least one of the first sensing material, the second sensing material, and the third sensing material comprises a dopant, as variously described herein. In another embodiment, a thickness of at least one of the first sensing material, the second sensing material, and the third sensing material is between about 100 microns to several centimeters. In another embodiment, the thickness of the first sensing material, the second sensing material, or the third sensing material is configured to increase a response time, an input dynamic range, output dynamic range, and/or a sensitivity of the first sensor, the second sensor, or the third sensor. In another embodiment, the first sensor, the second sensor, or the third sensor, may be fabricated using an electrospinning and/or spraying technique, in which case the thickness of the sensing material may be between approximately 100 nm to approximately 1 mm.

In another embodiment, (i) a cross-sectional shape of the electrodes or (ii) a spacing between two or more of the electrodes may be configured to increase a response time, an input dynamic range, output dynamic range, and/or a sensitivity of the first sensor, the second sensor, or the third sensor.

In another embodiment, a normal force acting on a portion of the first sensing material generates a compression of the first sensor and a tension on the third sensor. Further, the sensors may be configured to generate a bend signal, a pressure signal, and a stretch signal based on the compression and the tension.

Figure 3B:
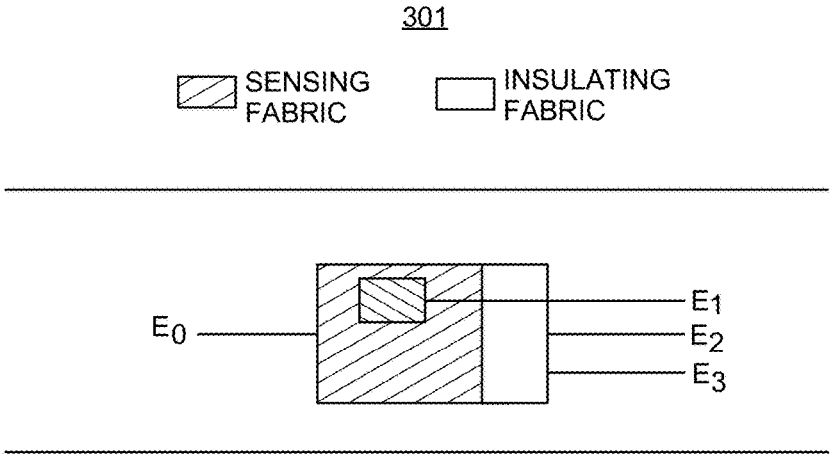
FIG. 3B shows a diagram of an overhead view of an example sensor, in accordance with example embodiments of the disclosure.

FIG. 3B shows a diagram of an overhead view of an example sensor, in accordance with example embodiments of the disclosure. In particular, the overhead view 301 includes a view of the electrical connection for the first electrode E1, the electrical connection for the second electrode E2, the electrical connection for the third electrode E3, and the electrical connection for the forth (common wire) electrode E0. Moreover, a view of the insulating fabric is also shown from the overhead view.

Figure 3C:
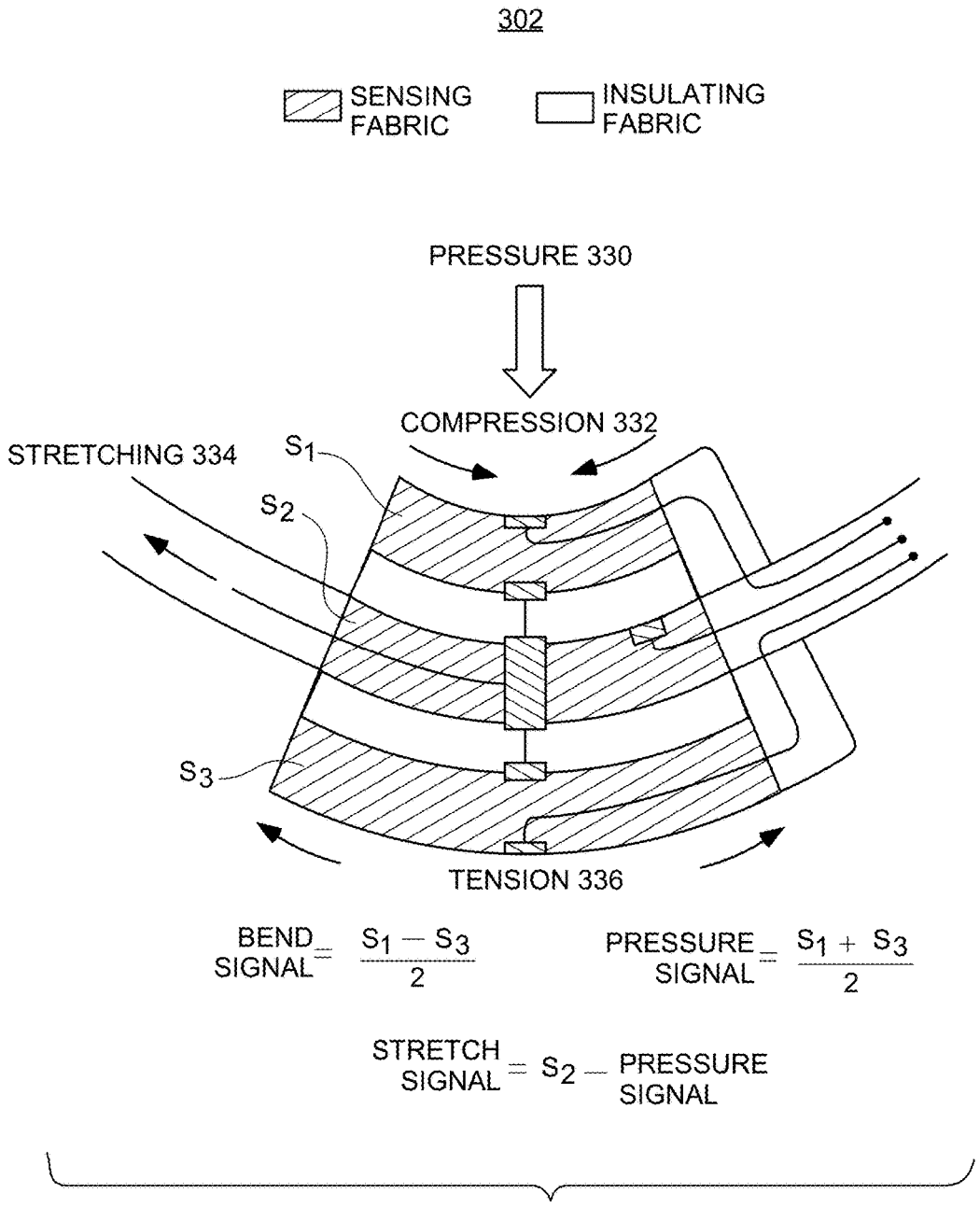
FIG. 3C shows a diagram of a cross-sectional view of signals generated by an example sensor, in accordance with example embodiments of the disclosure.

FIG. 3C shows a diagram 302 of a cross-sectional view of signals generated by an example sensor, in accordance with example embodiments of the disclosure. In various aspects, the resistivity of the sensing material (e.g., the fabric) may be configured to correspond with the expected pressure load to measure with a sensor. In another embodiment, perturbations, such as pressure, may results in a change of a material parameter (e.g., resistance) of one or more portions of the pressure sensors, and this change of material parameter can be measured to determine an output of the electronic device.

In particular, the sensors in device 302 may be configured to detect one or more of a pressure 330, a compression 332, a stretching 334, tension 336, and combinations thereof. In another embodiment, the sensors in device 302 may have sensing orthogonality properties. For example, in order to measure pressure 330 while avoiding measuring bending during a pressure measurement of a given area, two pressure sensors may be placed above and below the given area. In another embodiment, the compression 332 and tension 336 forces that may contribute to bending in the given area may be measured by the two pressure sensors, respectively, and subtracted from one another (e.g., by a computational module including memory and at least one processor), as shown in equation (4), below. Accordingly, because the two signal changes due to pressure 330 may have a similar magnitude but may have a sign difference (e.g., corresponding to the fact that the given area may exhibit a lower resistivity for a compressive force, and higher resistivity for a tension force), the pressure on the given area may be computed as the average of the two sensor values, as shown in equation (3), below. In another example, in order to avoid making unwanted stretching measurements, at least portions of the electronic device and/or portions of the garment may include conductive fabrics that are laced with non-stretch fibers. Alternatively, or additionally, the conductive fabrics may be sewn onto at least a portion of a non-stretch garment.

In various embodiments, the sensor may include one or more additional sensors (S1 and S3) configured to detect bending (which may be referred to as bend sensors herein). In another embodiment, the construction of such bend sensors may include placing conductive material (e.g., fabric) between two identical materials (e.g., fabric or another flexible substrate). Further, the electronic device may feature a design such that the conductive fabrics are placed at a neutral axis of the electronic device (e.g., as further shown and described in connection with element 348 of FIG. 3D, below).

As noted, in another embodiment, the sensors (S1, S2, and S3) may have a sensing orthogonality property. For example, in order to avoid making an unwanted pressure 330 measurement on a given area, a first cushion material may be positioned atop the sensing material of one of bend sensors S1, for example, in order to bear and dissipate the loaded pressure before contacting and impacting the sensing material. In another embodiment, a bend sensor S2 positioned on the neutral axis of the electronic device may increase resistance, while applied pressure reduces resistance. Therefore, bend sensing and pressure sensing can be distinguished based at least in part on a sign change associated with the resistance measurement of the given area.

Further, two pressure sensors may be positioned equidistant above and below the neutral axis of an electronic device. Further, the measured values of the pressure sensors can be subtracted to isolate the bending component (e.g., due to compression and tension) and to remove the equivalent pressure component. Accordingly, the following equations may be shown to hold:

$$\text{Sensor}_{(compression)}=P+B \tag{1}$$

$$\text{Sensor}_{(tension)}=P-B \tag{2}$$

$$P=(\text{Sensor}_{(compression)}\pm\text{Sensor}_{(tension)})/2 \tag{3}$$

$$B=(\text{Sensor}_{(compression)}-\text{Sensor}_{(tension)})/2 \tag{4}$$

$$S=\text{Sensor}_{(stretch)}-P \tag{5}$$

where P, B, and S are the pressure, bend, and stretch values, respectively.

In various embodiments, the electronic devices may include one or more sensors configured to detect stretching (which may be referred to as stretch sensors herein). In another embodiment, the construction of such stretch sensors may include a single layer including a conductive material (e.g., conductive fabric) that may have a relatively minimal thickness (e.g., about 1 mm thick or less). Alternatively, the construction of such stretch sensors may include a thick conductive fiber with relatively high stretch and compression capabilities. In various embodiments, the electronic device may include sensors that have an orthogonality property. For example, the electronic device may include a single sheet, or a minimally thin fabric that may not deform or bend if force is applied perpendicular to its surface area. Accordingly, stretching may only cause extension of fibers, thereby changing resistance of the electronic device. In another embodiment, for electronic devices including thick conductive fibers with relatively high compression and stretch capabilities, the capacitance, rather than the resistance, may be measured. For example, conductive pads may be added to the electronic device, the conductive pads having defined surface areas, and may be positioned at the above and below the fabric. Further, the capacitance may be measured using the formula: $C=E_0A/d$, where capacitance C is in units of Farads. Accordingly, stretching thicker conductive fabrics may increase capacitance, C, as d decreases, as can be demonstrated by the above formula.

In various embodiments, the electronic device may include one or more sensors having a particular design based at least in part on the sensing mechanism. In one embodiment, the sensors may include components such as a conductive material (e.g., a conductive fabric), conductive traces having positive and negative terminals that can serve to measure various electronic parameters (e.g., voltage, current, resistance, capacitance, and/or inductances), and an insulating material for example, as an outer layer.

In various aspects, the density of fibers, and conductivity of fibers, and ratio or mixture of conductive to non-conductive fibers in a material (e.g., a fabric) used in a sensor of an electronic device may be proportional to the conductivity of the material (or inversely proportional to the resistance of the material). In particular, resistance is defined as $R=\rho l/A$ in units of Ohms (Ω), where l is the length, A is the cross-sectional area, and ρ is the resistivity of the material (intrinsic to the material such as fabric).

Figure 3D:
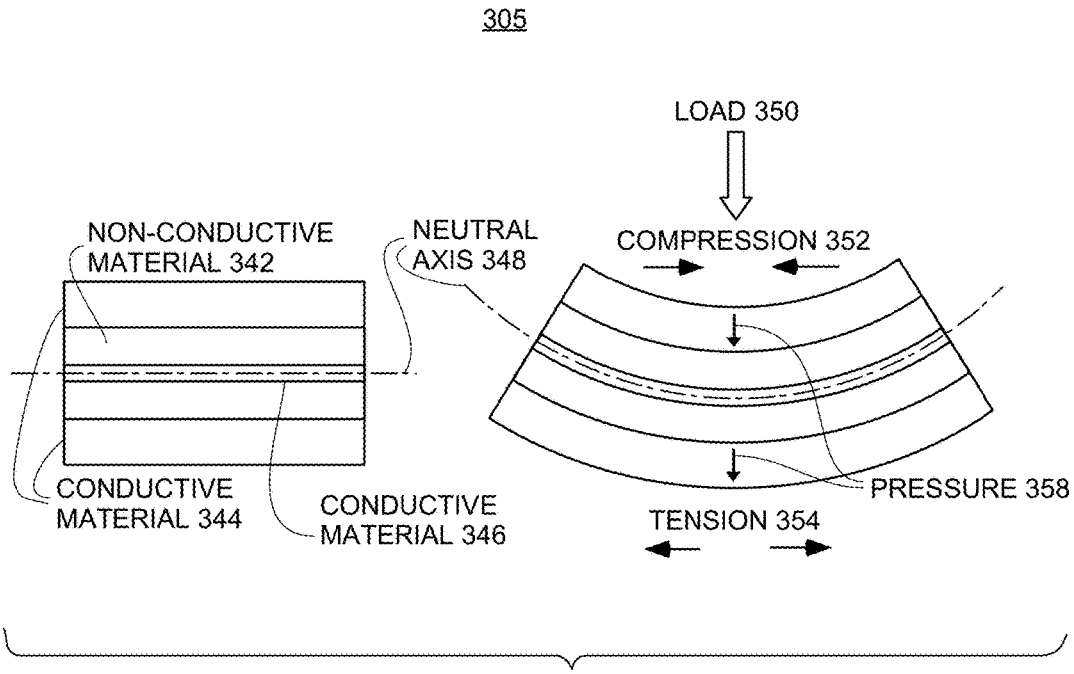
FIG. 3D shows a diagram of another cross-sectional view of signals generated by an example sensor, in accordance with example embodiments of the disclosure.

FIG. 3D shows a diagram of another cross-sectional view of signals generated by an example sensor, in accordance with example embodiments of the disclosure. In various embodiments, diagram 305 shows conductive fabric 344 that may be implemented in an electronic device (not shown). The electronic device may be used to independently discern the effects of pressure 358 as well as tension 354 and compression 352. In one embodiment, a load 350 may cause lateral and/or longitudinal deformation, which may generate pressure in the electronic device. This may be sensed by the top and bottom materials of the electronic device (e.g., non-conductive fabric 342, the conductive fabric 344) above and below the embedded conductive fabric 346. Further, bending may be sensed by the embedded conductive fabric 346 along a neutral axis 348 region of the electronic device. In another embodiment, stretching can be measured by the electronic device by measuring the capacitance change between the top and bottom materials fabrics (e.g., non-conductive fabric 342, the conductive fabric 344), or by sensing a resistance change along the middle conductive fabric 346.

Figure 4:
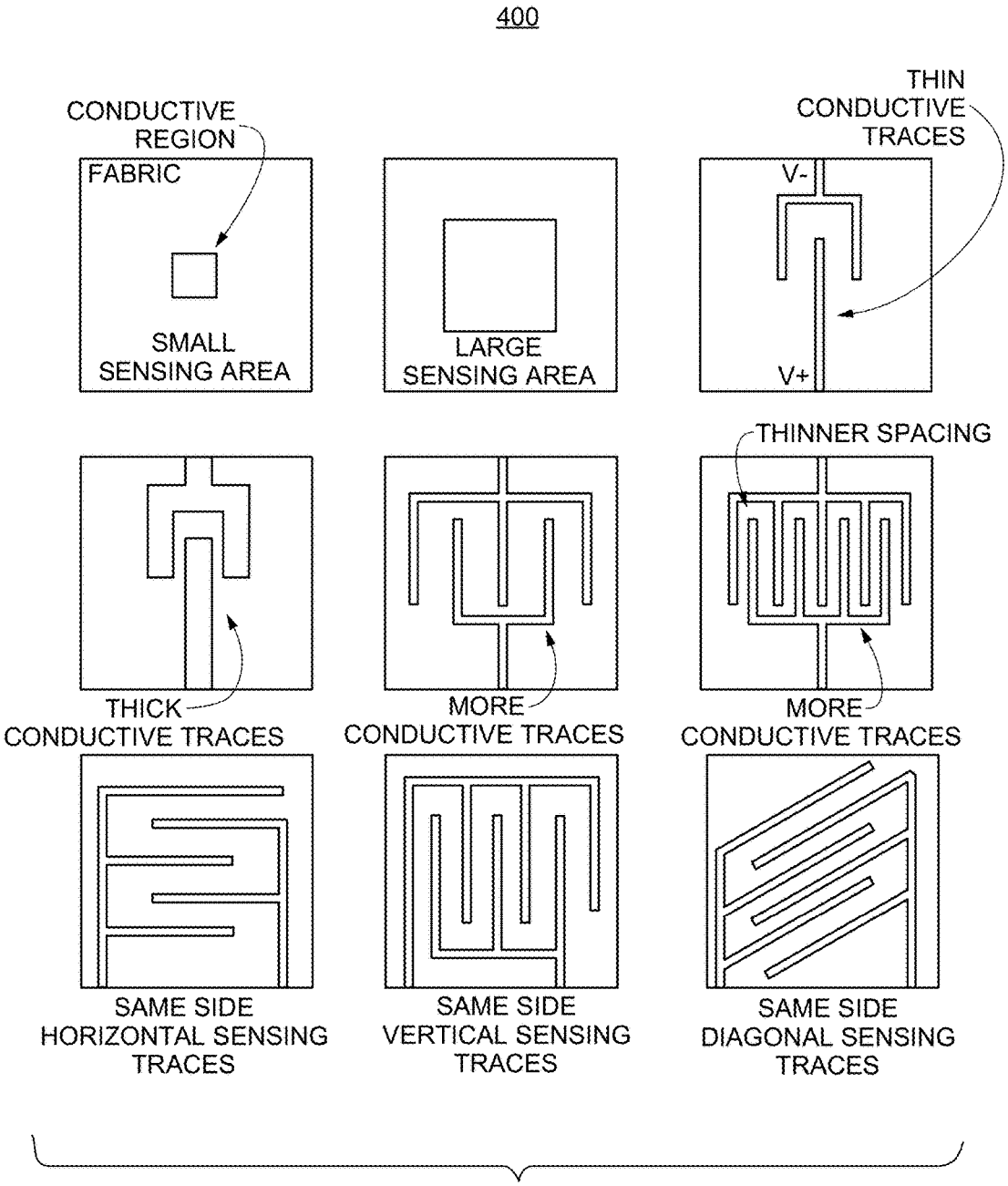
FIG. 4 shows diagrams illustrating different sensing geometries that may be used to detect various parameters (e.g., voltage, current, resistance, capacitance, inductance), in accordance with example embodiments of the disclosure.

FIG. 4 shows diagrams 400 illustrating different sensing geometries that may be used to detect various parameters (e.g., voltage, current, resistance, capacitance, inductance), in accordance with example embodiments of the disclosure. As noted, the sensors may be fabricated using conductive materials such as conductive fabric. Further, the dimensions and the layout of conductive traces on conductive material may affect the characteristics of an electronic device's output. In one embodiment, as noted, the disclosed electronic devices may include pressure sensors that may include a material such as fabric that is made using a conductive material.

In one embodiment, a distortion in a group of fibers of a sensor may alter the compaction or tension of neighboring fibers, altering fiber density thereby changing resistance. In another embodiment, applying pressure or weight onto a material having fibers (e.g., fabric) may reduce the distance between adjacent conductive fibers of the sensor, reducing resistance of the sensor. In one embodiment, bending a sensor along a compression zone of the sensor may reduce the distance between adjacent conductive fibers of the sensor, and thereby reduce the resistance of the sensor. In one embodiment, bending the sensor along a tension zone of the sensor may increase the distance between adjacent conductive fibers of the sensor, and thereby increase the resistance of the sensor. In another embodiment, bending the sensor along a neutral axis of the sensor may increase the resistance as the length of the fibers of the sensor increase.

In various embodiments, stretching of the sensor of an electronic device may lead to various changes in the parameters of the sensor, as described below. In particular, if the stretching occurs along a fiber axis (e.g. parallel to the seams) of the sensor, the fibers of the sensor may be elongated, and adjacent fibers of the sensor may be compressed together. Accordingly, the differences in stretching of the sensor and compression of the sensor may serve as opposing effects in the sensor. Further, resistance of the sensor can either increase or decrease depending on the conductivity of the fibers of the sensor, the thickness of the fibers of the sensor, the stretch-ability of fibers, and density of fibers of the sensor, combinations thereof, and/or the like. In another embodiment, if the stretching occurs perpendicular to the fiber axis (e.g. perpendicular to the seams) of the sensor, the fibers of the sensor may be separated from each other, thereby increasing the resistance of the sensor.

In various embodiments, several techniques may be used to tune the sensitivity of the disclosed sensors used in the electronic devices, as described below. In particular, changing the conductivity of the material comprising the sensor (e.g., fabric) may change the sensitivity of the sensors. In another embodiment, changing the density of weaved fibers in the sensor material (e.g., the fibers of a conductive fabric) may change the sensitivity of the sensors. Further, changing the thickness of the conductive coating on the sensor material (e.g., the conductive coating of a fabric) may change the sensitivity of the sensors. In another embodiment, changing the ratio of weaved conductive fibers of a conductive material to the non-conductive fibers of a non-conductive material may change the sensitivity of the sensors. In one embodiment, changing the type of conductive material deposited onto a sensor material (e.g., a fabric) may change the sensitivity of the sensors. In another embodiment, the method of fabricating the sensors and constituent materials (e.g., via various deposition techniques) and various process parameters may serve to change the sensitivity of the sensors. In another embodiment, the type and number of layers of conductive materials (e.g., fabrics) that may be weaved together may change the sensitivity of the resulting sensors.

In various embodiments, various properties of conductive traces of the electronic devices and associated sensors may be modified to change the sensitivity of the sensors. In particular, the spacing between negative and positive leads of the sensors of the electronic device may be modified to change the sensitivity of the sensors. In another embodiment, the contact area of the negative lead and positive lead of the sensors of the electronic device may be modified to change the sensitivity of the sensors. In one embodiment, the number of interdigitated negative and positive leads of the sensors of the electronic device may be modified to change the sensitivity of the sensors as shown in FIG. 4.

In various embodiments, various trends related to parameters associated with the sensors may be used to optimize sensor performance. For example, increasing the density of conductive fibers of the material of a sensor may reduce the resistance of the sensor. In another embodiment, increasing the thickness of the conductive coating on a sensor material (e.g., fabric) may reduce the resistance of the sensor material. In one embodiment, increasing the ratio of conductive to non-conductive materials (e.g., conductive fabrics) in the sensor material may reduce the resistance of the sensor material. In various embodiments, layering more conductive material such as conductive fabrics may reduce the resistance of a sensor. In another embodiment, increasing the spacing between negative and positive leads of a sensor may increase the measured resistance of the sensor. In one embodiment, increasing the contact area of the negative or positive leads of a sensor may reduce the measured resistance of the sensor. In another embodiment, increasing the number of interdigitated negative and positive leads of the sensor may reduce the measured resistance of the sensor.

Figure 5:
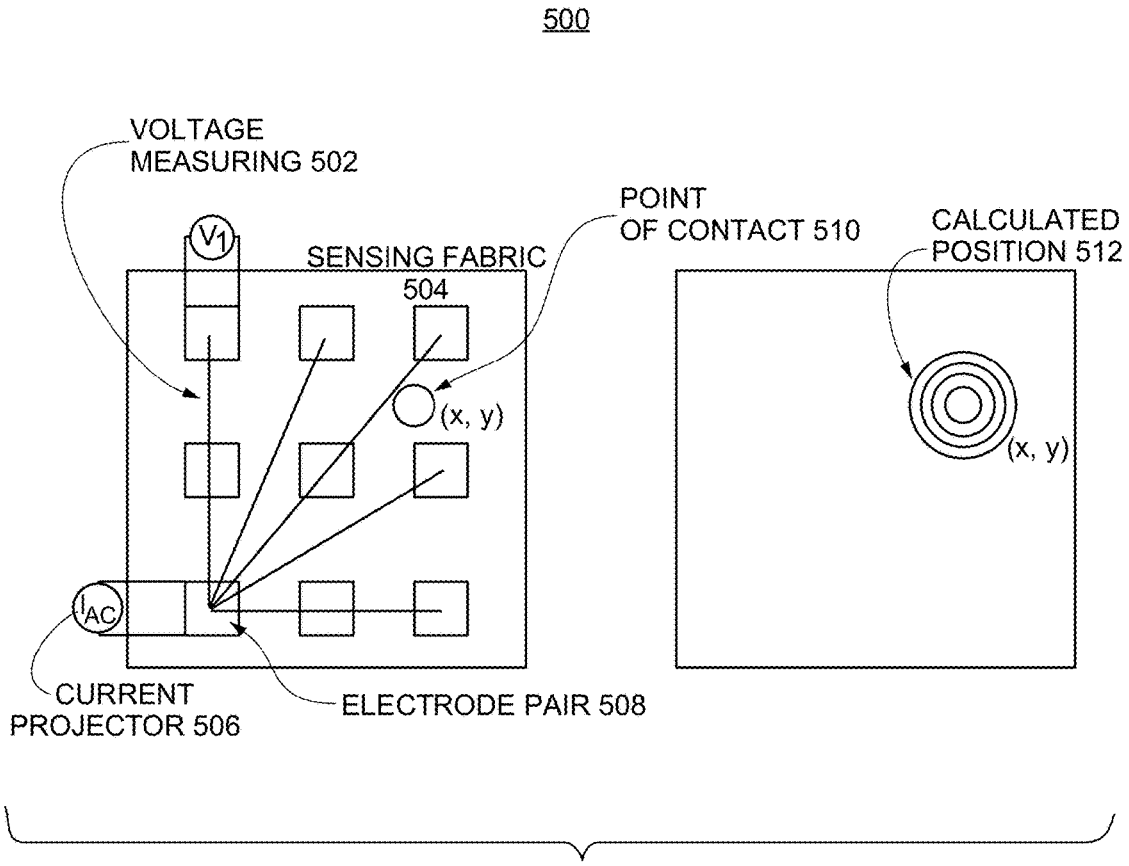
FIG. 5 shows a diagram illustrating the placement of electrodes on a sensing material (e.g., fabric), in accordance with example embodiments of the disclosure.

FIG. 5 shows a diagram illustrating the placement of electrodes on a sensing material (e.g., fabric), in accordance with example embodiments of the disclosure. In various embodiments, one sensing technique that may be implemented as will be shown by diagram 500 may include an electronic device having sensors may include an electric field tomography (EFT) technique. In particular, neighboring sensing electrodes are used to emit a small AC current. The neighboring electrode pair may be referred to as a current-projecting pair. In another embodiment, voltage differences may be measured across all adjacent electrode pairs in the sensing material of a sensor. The adjacent electrode pairs may be referred to as voltage-measuring pairs. In another embodiment, a mesh of cross-sectional measurements may be used to determine a location on the sensing material that corresponds to a local shunting of the resistance level, for example, based on a user's touch.

In particular, as shown in diagram 500 the electrode pair 508 may be placed externally or internally on a portion of an electronic device comprising a sensing material 504 such as a conductive fabric. Further, an electrode pair (e.g., any two electrodes 508 shown in diagram 500) may be used to emit a signal (e.g., an AC current using a current projector 506), which may then be measured across the remaining electrode pairs of the electronic device (e.g., measured using a voltage measuring unit 502). This process may be repeated in series or in parallel using the remaining electrodes of the electronic device thereby creating a network of signals which can be used to determine the location (e.g., a calculated position 512) of a perturbation (e.g., a touch resulting from a point of contact 510) on the sensing material.

Figure 6:
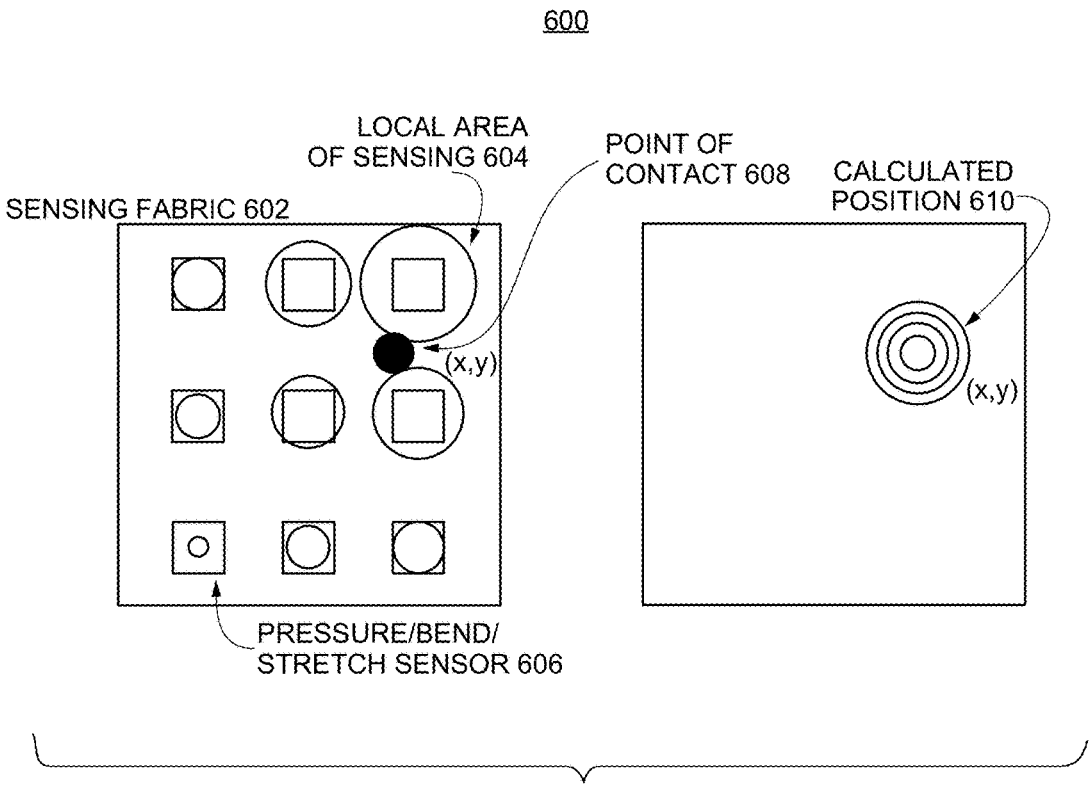
FIG. 6 shows another diagram illustrating the placement of electrodes on a sensing material (e.g., fabric), in accordance with example embodiments of the disclosure.

FIG. 6 shows another diagram illustrating the placement of electrodes on a sensing material (e.g., fabric), in accordance with example embodiments of the disclosure. In an embodiment, an electric impedance tomography (EIT) technique may be implemented to determine the location of the perturbation on the sensing material. For example, one or more electrode pairs on the electronic device may measure the local resistance of the region they are on the sensor. Further, a matrix of resistance measurements may be made by arranging the electrode pairs on a single-sheet of conductive material. In one embodiment, a perturbation to the conductive material (e.g., a conductive fabric) may result in a local resistance change, which may be measured by the matrix of electrodes. In various embodiments, the coordinates of each electrode, along with their measurement value may be used to locate the precise area of perturbation.

In particular, as shown in diagram 600, electrode pairs and related pressure/bend/stretch sensors 606 may be used to measure the local resistance in a local area of sensing 604 either from one or more of a deformation of the sensing material 602 resulting from one or more of an applied pressure, bending force, stretching force, combinations thereof, and/or the like. In another embodiment, the local sensing area 604 may be used to triangulate (e.g., determine a calculated position 610) the location of perturbation (e.g., point of contact 608) on the sensing material 602.

Figure 7:
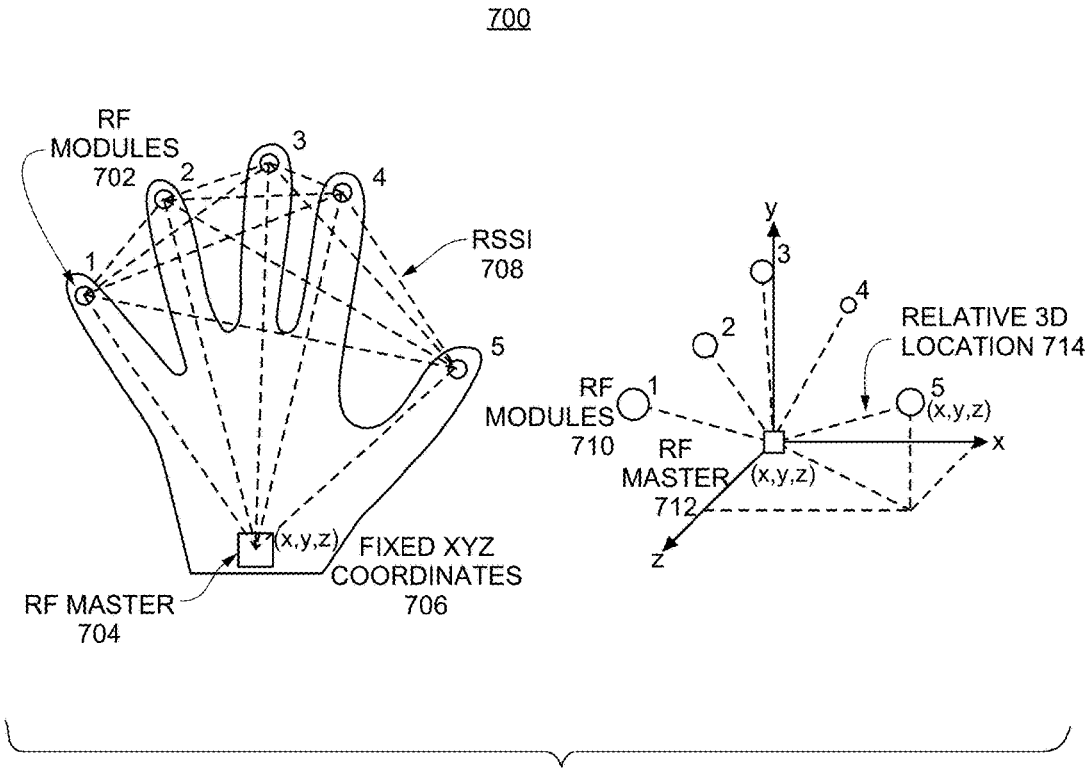
FIG. 7 shows an example diagram of an application of the electronic devices described herein, in accordance with example embodiments of the disclosure.

FIG. 7 shows an example diagram of an application of the electronic devices described herein, in accordance with example embodiments of the disclosure. In another embodiment, a radio frequency distance tomography (RFDT) technique may be implemented to determine the location of various position of a body part. In particular, RF transceiver devices are fixated on certain areas of clothing. In one embodiment, the devices may include inertial measurement units (IMUs). In another embodiment, a master RF transceiver device may be positioned on a location that does not move relative to the other RF modules of the assembly. Further, RSSI signal may be captured from all other RF signal generators of the other RF devices, yielding a distance measurement between devices. Further, the RSSI values may be sent to the master RF transceiver device, where a mesh network of RSSI values may be calculated to determine the relative position of each RF module to the master RF module.

In particular, diagram 700 shows an application of an assembly of electronic devices in tracking a body part of a user, such as the hand of a user. In another embodiment, a first (master) radio frequency (RF) device/module 704 may be placed on the wrist, as an example, which may serve as a fixed reference point 706 for the assembly. Moreover, a plurality of RF modules/devices 702 may be coupled to the fingers, or any portion of the body of the user. Further, received signal strength indication (RSSI) signals 708 may be generated and read from each RF device on the fingers. In another embodiment, the RSSI signals 708 may be transferred to the RF device 704, which may then determine (e.g., via triangulation) the relative position 714 of each RF device 710 relative to the first RF device 712.

Figure 8:
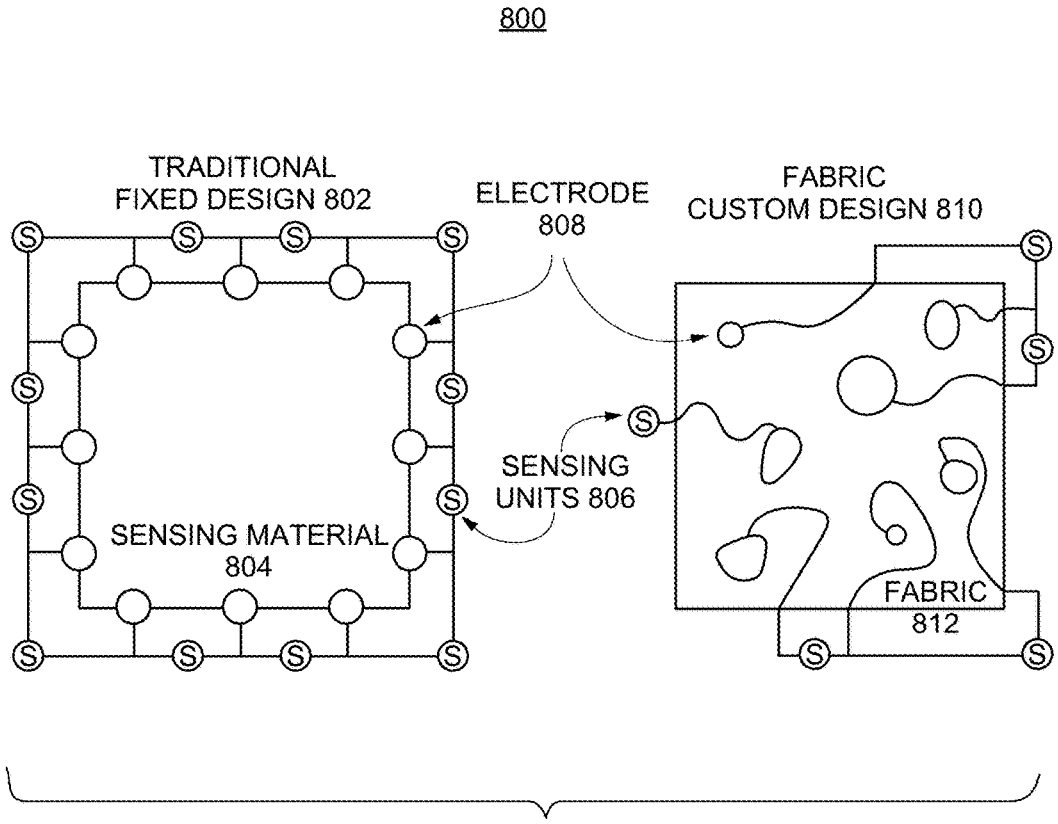
FIG. 8 shows a diagram of electrode arrangements with respect to a sensing material, in accordance with example embodiments of the disclosure.

FIG. 8 shows a diagram 800 of electrode 808 arrangements with respect to a sensing material 804, in accordance with example embodiments of the disclosure. In particular, a traditional configuration 802 of sensing units 806 and electrodes 808 is shown and an alternative custom design 810 of sensing units 806 on fabric 812 (e.g., another sensing material example) is shown.

In particular, in one embodiment, as shown in diagram 802, design constraints may lead to the electrodes being placed on the exterior of the sensing material 804 in connection with the sensing units 806 of an electronic device. In another embodiment 810, using various fabric design tools such as vinyl cutting tools, or sewing electrodes can be irregularly placed with custom dimensions in order to control for sensitivity and adjust for local area effects in garments (such as extra layers, different materials, combinations thereof, and/or the like).

In various embodiments, as noted, the electrodes 808 can be fabricated in different topologies and arrangements using vinyl cutting techniques, embroidery of conductive fabrics, using thin-sheet conductive metals, combinations thereof, and/or the like. In another embodiment, the sensing material 804 may include fabric, rather than metal sheets, conductive polymers, or glass. In one embodiment, the electrodes 808 may not need to be on the perimeter of the sensing conductive material. Rather, the electrodes 808 can be made to contact internal areas of the sensing conductive material. In various embodiments, the intensity of the signals can be weighted depending on various electrode parameters including, but not limited to, the size, conductivity, and surface area of the electrode. Such parameters may be controlled using computerized techniques including, but not limited to, vinyl cutting or CNC embroidery.

Figure 9:
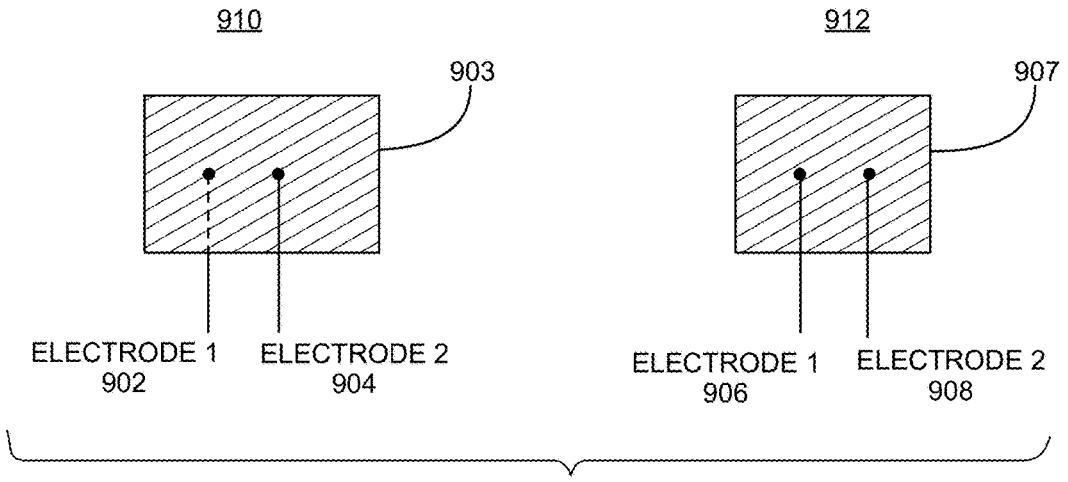
FIG. 9 shows diagrams depicting different configurations for the electrode leads associated with a given portion of the sensor, in accordance with example embodiments of the disclosure.

FIG. 9 shows diagrams depicting different configurations for the electrode leads associated with a given portion of the sensor, in accordance with example embodiments of the disclosure. In particular, in a first embodiment as shown in diagram 910, the sensor may include a first electrode 902 that may be placed below a sensing material 903, and a second electrode 904 that may be placed above the sensing material 903. In another embodiment as shown in diagram 912 the sensor may include a configuration where the first electrode 906 and the second electrode 908 are both placed above or below the sensing material 907.

Figure 10:
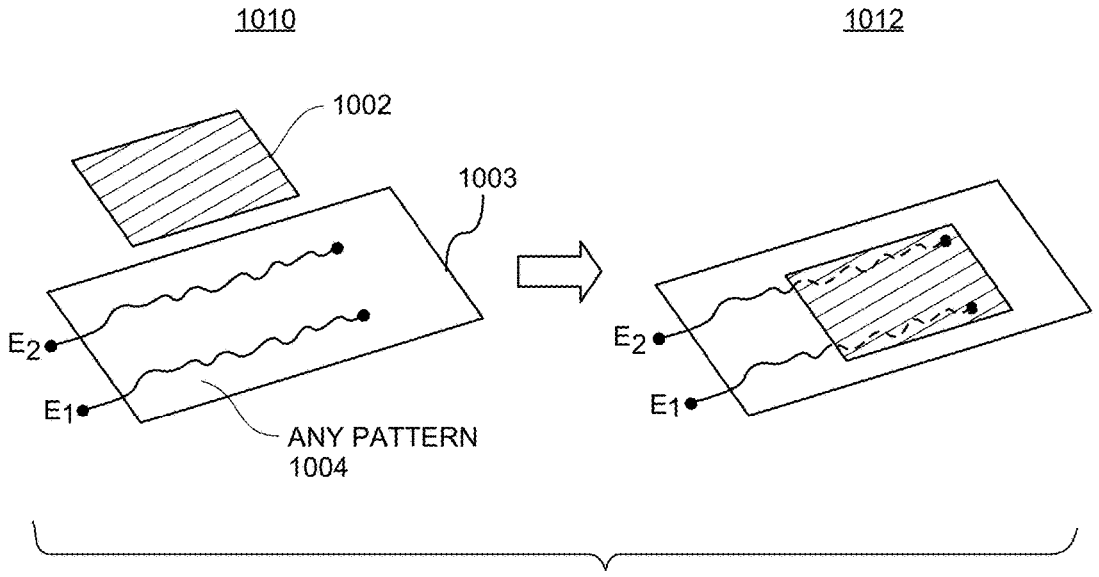
FIG. 10 shows diagrams that describe the coupling of a sensing material and a portion of an article of clothing, in accordance with example embodiments of the disclosure.

FIG. 10 shows diagrams that describe the coupling of a sensing material and a portion of an article of clothing, in accordance with example embodiments of the disclosure. In a first embodiment, diagram 1010 shows the sensing material 1002 (e.g., a sensing material including a conductive fabric). Further, diagram 1010 shows the portion of clothing 1003. Moreover, the leads for the first electrode E1 and the second electrode E2 may be formed on the portion of clothing in any suitable pattern, such as the pattern 1004 shown in diagram 1010. Moreover, as shown in diagram 1012, the sensing material 1002 may be coupled (e.g., mechanically coupled) to the portion of clothing 1003, at least partially enclosing the electrodes E1 and E2. In one example, the sensing material 1002 may be configured to be sown onto the portion of clothing 1003, for example, along the periphery of the portion of clothing 1003. In an embodiment, the sensing material 1002 may be made of an suitable material such that it can be laminated (e.g., ironed) onto the portion of clothing with the application of heat, pressure, or both. In yet another embodiment, the sensing material 1002 may be coupled to the portion of clothing 1003 using any suitable technique including combinations of sewing and lamination, or the like.

FIG. 11A shows diagrams that describe another aspect of the coupling of a sensing material and a portion of an article of clothing, in accordance with example embodiments of the disclosure. In a first embodiment, diagram 1101 shows the sensing material 1102 (e.g., a sensing material including a conductive fabric). Further, diagram 1101 shows a first portion of clothing 1104 and a second portion of clothing 1106. Moreover, the leads for the first electrode E1 and the second electrode E2 may be formed on the first portion of clothing 1104 and the second portion of clothing 1106, respectively, the electrode leads having any suitable pattern.

As shown in diagram 1103, the sensing material 1102 may be coupled (e.g., mechanically coupled) to the first portion of clothing 1104, at least partially enclosing electrode E1. In one example, the sensing material 1102 may be configured to be sown onto the first portion of clothing 1104, for example, along the periphery of the first portion of clothing 1104. In an embodiment, the sensing material 1102 may be made of any suitable material such that it can be laminated (e.g., ironed) onto the portion of clothing with the application of heat, pressure, or both. In yet another embodiment, the sensing material 1102 may be coupled to the first portion of clothing 1104 using any suitable technique including combinations of sewing and lamination, or the like. Additionally, the first portion of clothing 1104 and the second portion of clothing 1106 may be positioned across a fold 1108.

As shown in diagram 1105, the sensing material 1102 may be sandwiched between the first portion of clothing 1104 and the second portion of clothing 1106 after folding 1109 the second portion of clothing 1106 over the fold 1108 of diagram 1103, as indicated in diagram 1105. The folding 1109 may be performed by a machine or by a human, using any suitable technique.

As shown in diagram 1107, the result of the folding 1109 that occurs in diagram 1105 may result in a structure having the cross-sectional view depicted in the diagram. In particular, the diagram 1107 shows that the sensing material 1102 may be sandwiched between the second portion of clothing 1106 and the first portion of clothing 1104. Moreover, the electrodes E1 and E2 are shown; in particular, the first electrode E1 may be configured between the second portion of clothing 1106 and the sensing material 1102, while the second electrode E2 may be configured between the sensing material 1102 and the first portion of clothing 1104.

Figure 11B:
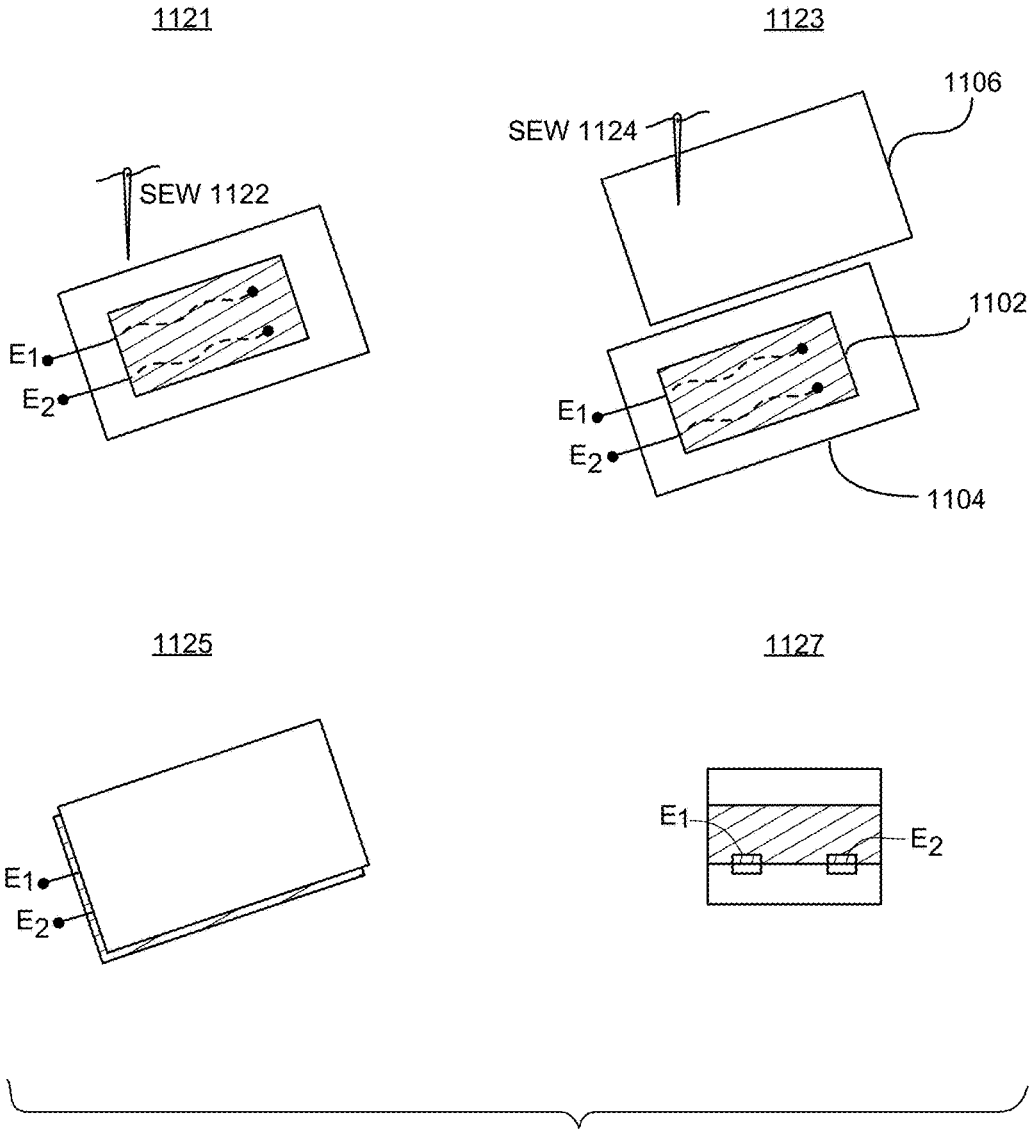

FIG. 11B shows diagrams that describe yet another aspect of the coupling of a sensing material and a portion of an article of clothing, in accordance with example embodiments of the disclosure. In particular, diagram 1121 shows the sensing material 1102 (e.g., a sensing material including a conductive fabric) that may be sewn 1122 onto a first portion of clothing 1104. Moreover, the leads for the first electrode E1 and the second electrode E2 may be formed on the first portion of clothing 1104, the electrode leads having any suitable pattern. Diagram 1123 shows the second portion of clothing 1106 that may be coupled to the first portion of clothing 1104 having the sensing material 1102, for example, by sewing 1124. Accordingly, diagram 1125 shows one perspective view of the final structure of the sensor, where the sensing material 1102 has been sandwiched by the first portion of clothing 1104 and the second portion of clothing 1106. Additionally, diagram 1127 shows that the sensing material 1102 may be sandwiched between the second portion of clothing 1106 and the first portion of clothing 1104. Moreover, the electrodes E1 and E2 are shown; in particular, the first electrode E1 and the second electrode may be configured between sensing material 1102 and the first portion of clothing 1104.

Figure 11C:
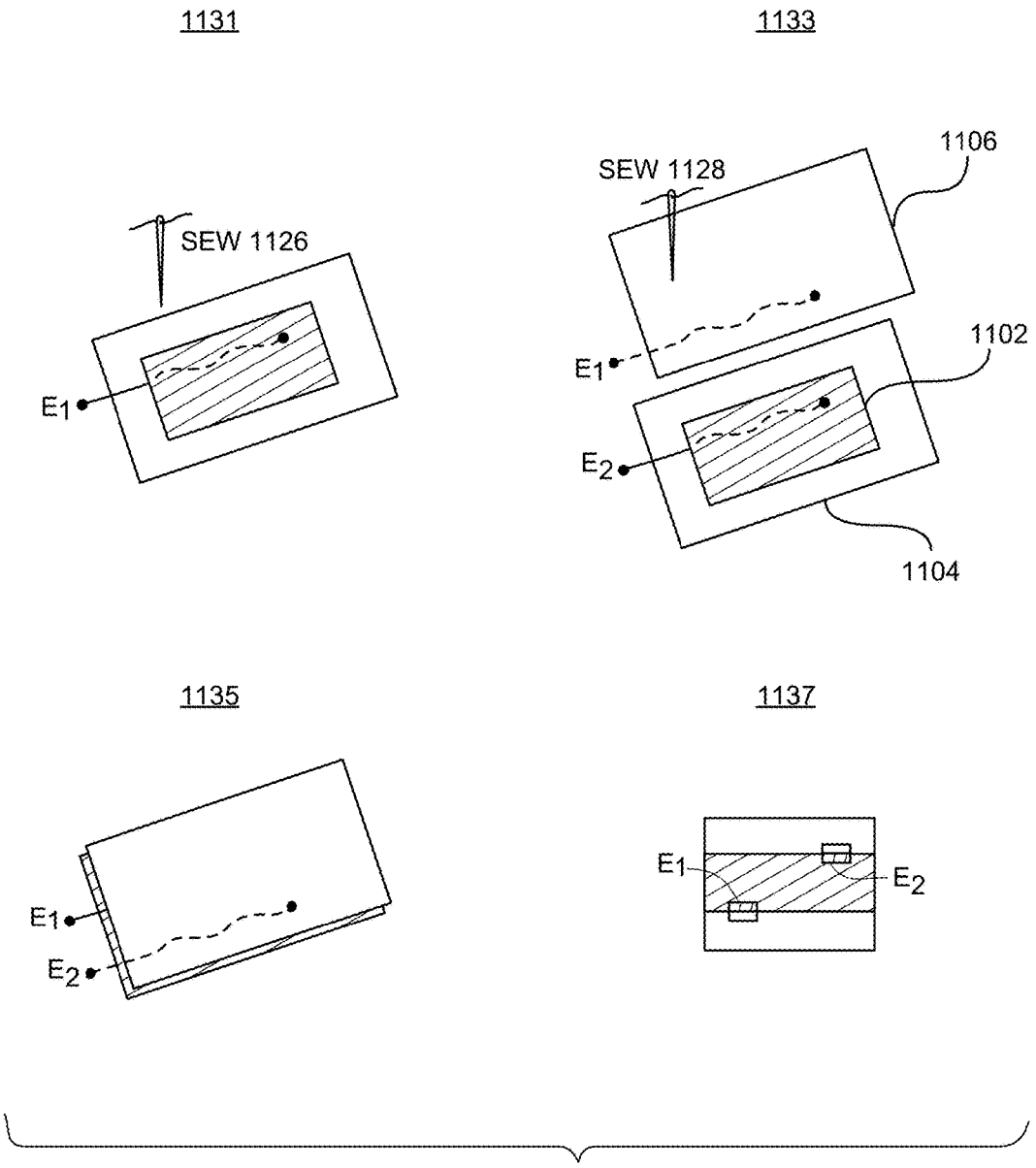

FIG. 11C shows diagrams that describe yet another aspect of the coupling of a sensing material and a portion of an article of clothing, in accordance with example embodiments of the disclosure. In contrast to the diagrams of FIG. 11B, the diagrams of FIG. 11C show a configuration where the electrodes are placed vertically apart instead of horizontally apart. Additionally, the sensors may be offset from one another (e.g., not necessarily be aligned on a vertical plane). In particular, diagram 1131 shows the sensing material 1102 (e.g., a sensing material including a conductive fabric) that may be sewn 1126 onto a first portion of clothing 1104. Moreover, the first electrode E1 may be formed on the first portion of clothing 1104, the first electrode lead having any suitable pattern. Diagram 1133 shows the second portion of clothing 1106 that may be coupled to the first portion of clothing 1104 having the sensing material 1102, for example, by sewing 1128. Accordingly, diagram 1135 shows one perspective view of the final structure of the sensor, where the sensing material 1102 has been sandwiched by the first portion of clothing 1104 and the second portion of clothing 1106. Additionally, diagram 1137 shows that the sensing material 1102 may be sandwiched between the second portion of clothing 1106 and the first portion of clothing 1104. Moreover, the electrodes E1 and E2 are shown; in particular, the second electrode E2 may be configured between the second portion of clothing 1106 and the sensing material 1102, while the first electrode E1 may be configured between the sensing material 1102 and the first portion of clothing 1104. As noted, the electrodes E1 and E2 may have a horizontal displacement from one another in addition to the vertical displacement.

Figure 12:
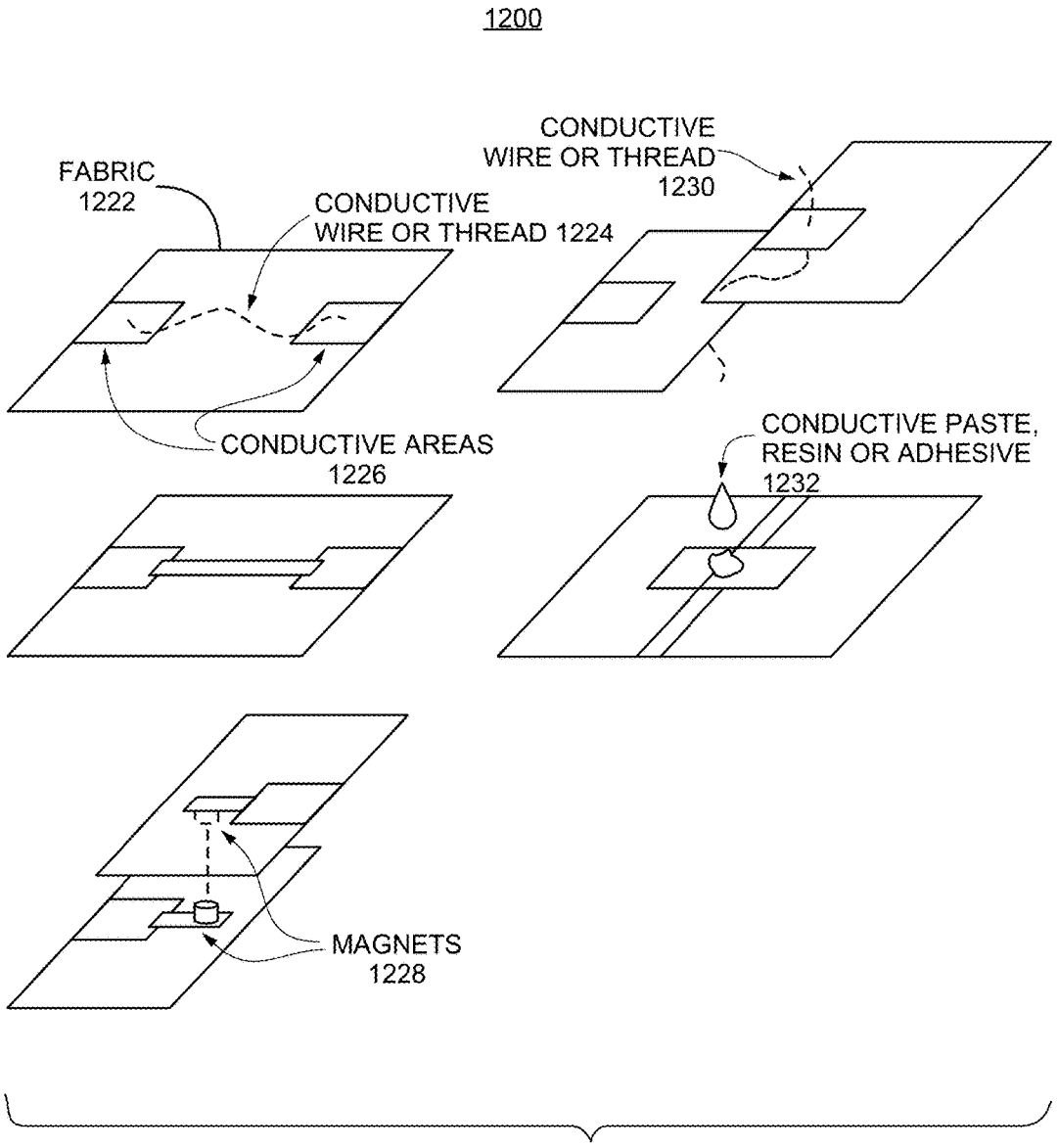
FIG. 12 shows diagrams of example connectors that may be used to electronically couple different regions of conductive materials (e.g., conductive fabrics), in accordance with example embodiments of the disclosure.

FIG. 12 shows diagrams 1200 of example connectors that may be used to electronically couple different regions of conductive or non-conductive materials 1222 (e.g., conductive fabrics), in accordance with example embodiments of the disclosure. For example, the diagrams illustrate example connectors that may be formed on conductive areas 1226 of the conductive materials. Further, the conductive areas 1226 may be electronically coupled to one another using conductive threads/wires 1224 and 1230, paste, resin or adhesives 1232, or embedded magnets 1228 that physically connect two adjacent areas.

In various embodiments, connectors may be used to form connection between areas within a given electronic device (e.g., between sensors of an electronic device), and/or between different electronic devices. In another embodiment, the connections can be directly stitched to the electronic device and/or the garment that the electronic device is a part of, for example, by using conductive threads and wires. In one embodiment, portions of conductive materials (e.g., conductive fabrics) can be electronically coupled using an adhesive (e.g., a fabric adhesive) sprayed with a conductive coating (e.g., a carbon-black material) in order to maintain an electrical connection. In another embodiment, any suitable material may be used to fuse the end of the connectors. For example, a blend of conductive epoxies can be used to fuse the ends of the connectors. In one embodiment, a blend of conductive paint can be used to fuse the ends of the connectors. Additionally, to maintain connection strength, uncured silicone resin can be applied onto portions of the conductive material (e.g., fabric). In particular, the silicone resin may diffuse between the conductive material as the material is cured. In various embodiments, magnets can be laced onto junctions or connections of at least portions of an electronic device, for example, at interfaces where external sensors and modules can be clipped onto the electronic device.

Figure 13:
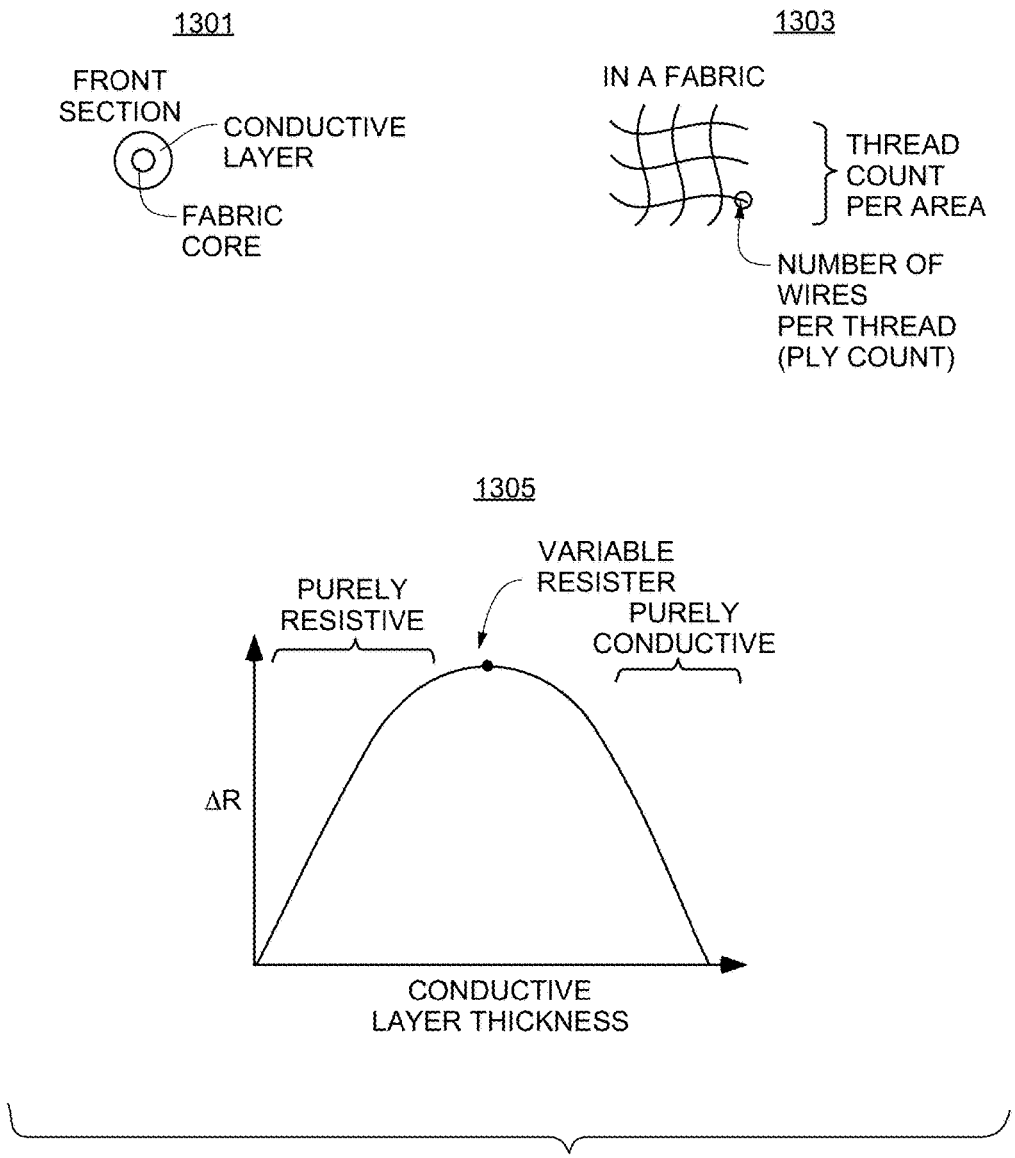
FIG. 13 shows a diagram including a plot of resistance versus conductive layer thickness, in accordance with example embodiments of the disclosure.

FIG. 13 shows a diagram including a plot of resistance versus conductive layer thickness, in accordance with example embodiments of the disclosure. In particular, diagram 1301 shows a front cross-section of a thread having a fabric core material enclosed by a conductive layer. Diagram 1303 shows the embedding of such a thread in a fabric, the fabric having a given thread count per unit area, and a number of wires per thread (e.g., ply count).

Diagram 1305 shows a plot of the change in resistance values of a given thread having the front cross-sectional area depicted in diagram 1301 versus the conductive layer thickness. In particular, as can be seen in diagram 1305, the change in resistance can have a first region that exhibits resistive characteristics, a second state that exhibits a variable resistance characteristics, which may correspond to a peak of the curve in diagram 1305, and a third state that exhibits a conductive resistive characteristics. Accordingly, the dimensions of the conductive thread may be optimized to have a suitable level of resistivity in order to generate a suitable measurement of force by the sensor.

Figure 14:
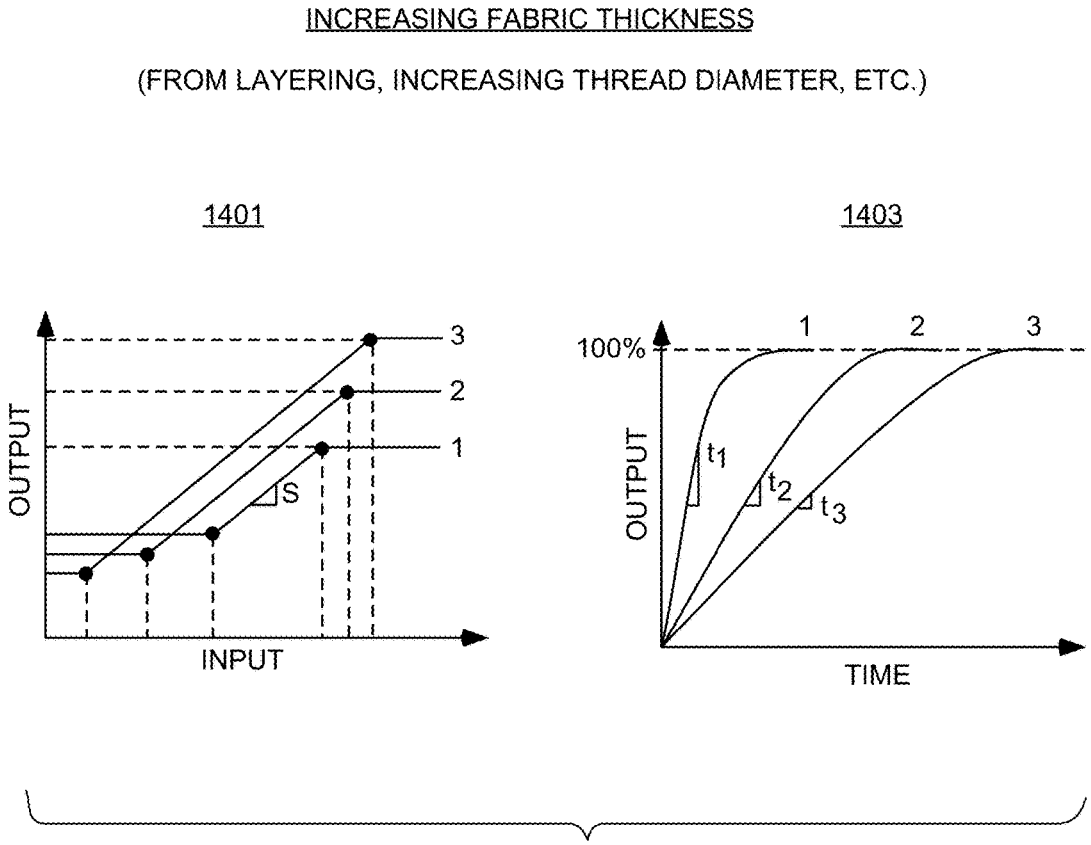
FIG. 14 shows a diagram of example plots of sensor characteristics with varying fabric thickness, in accordance with example embodiments of the disclosure.

FIG. 14 shows a diagram of example plots of sensor characteristics with varying fabric thickness, in accordance with example embodiments of the disclosure. In particular, diagram 1401 shows a unitless diagram of the trend for the output (e.g., output measurement) of the sensor versus the input (e.g., input force) for a given measurement quantity (e.g., force). Further, the plot of diagram 1401 indicates that for different inputs 1, 2, and 3 corresponding to increasing fabric thicknesses, respectively, the output of the sensor may have an increasing dynamic range, while maintaining a similar sensitivity (e.g., as represented by the slopes of the lines of diagram 1401). Diagram 1403 shows the general trends for the output (e.g., output measurement of the sensor (in units of percent) versus time (e.g., in a given unit of time such as milliseconds, depending on the exact geometry and materials of the sensor). Further, the plot diagram 1403 shows that for different inputs 1, 2, and 3 corresponding to increasing fabric thicknesses, respectively, the output of the sensor may have taken a longer time to reach its final value absent transients (e.g., value corresponding to 100% on the output y-axis) for the thicker material thicknesses in the device sensors than for thinner materials. In various embodiments, the thickness of the materials may be increased as a result of layering multiple materials, increasing the thread diameter (e.g., as shown and described in connection with FIG. 13, above), stacking sensor devices, combinations thereof, and/or the like.

Figure 15:
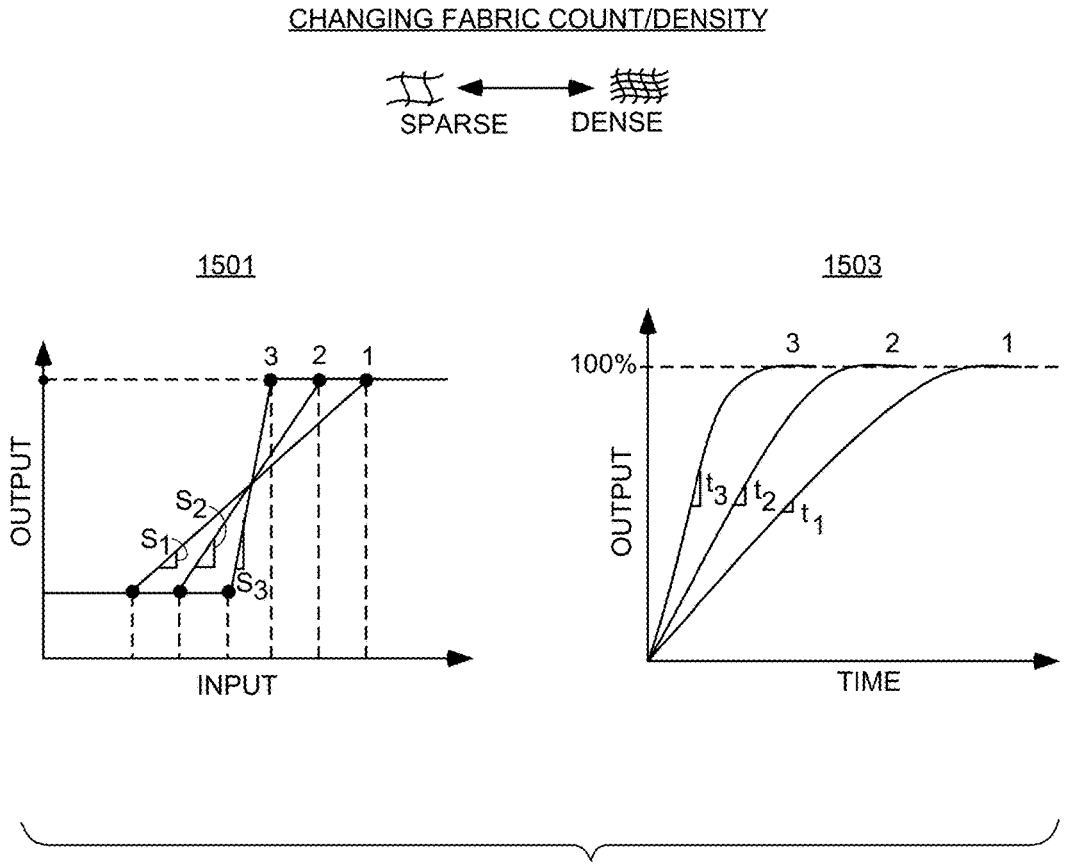
FIG. 15 shows a diagram of example plots of sensor characteristics with varying sensing material (e.g., conductive fabric) density (e.g., from sparse to dense), in accordance with example embodiments of the disclosure.

FIG. 15 shows a diagram of example plots of sensor characteristics with varying sensing material (e.g., conductive fabric) density (e.g., from sparse to dense), in accordance with example embodiments of the disclosure. In particular, diagram 1501 shows a unitless diagram of the trend for the output (e.g., output measurement) of the sensor versus the input (e.g., input force) for a given measurement quantity (e.g., force). Further, the plot of diagram 1501 indicates that for different inputs 1, 2, and 3 corresponding to increasing sensing material density, respectively, the output of the sensor may have an increasing sensitivity (e.g., represented by the slope of the lines diagram 1501), while maintaining a similar dynamic range. Diagram 1503 shows the general trends for the output (e.g., output measurement of the sensor (in units of percent) versus time (e.g., in a given unit of time such as milliseconds, depending on the exact geometry and materials of the sensor). Further, the plot diagram 1503 shows that for different inputs 1, 2, and 3 corresponding to increasing sensing material density, respectively, the output of the sensor may take a shorter time to reach its final value absent transients (e.g., value corresponding to 100% on the output y-axis) for the denser sensing materials in the device sensors than for less dense sensing materials.

Figure 16:
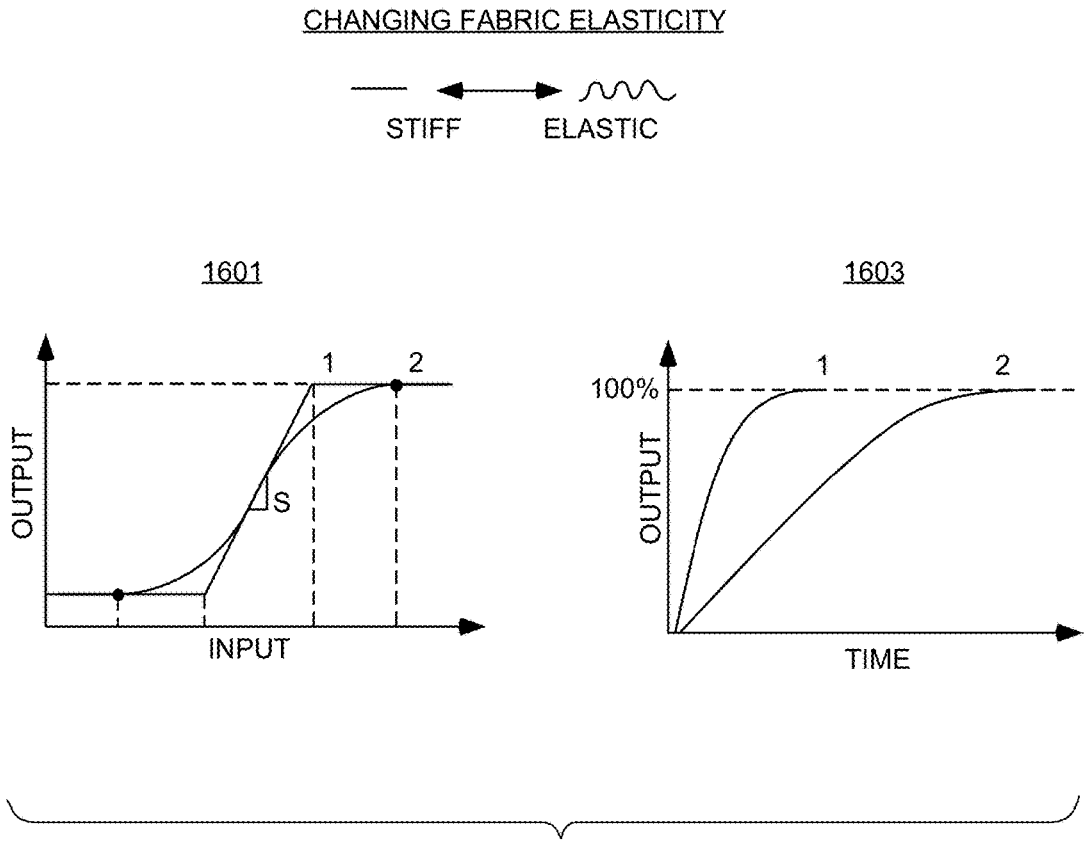
FIG. 16 shows a diagram of example plots of sensor characteristics with varying sensing material (e.g., conductive fabric) elasticity (e.g., from relatively stiff to elastic), in accordance with example embodiments of the disclosure.

FIG. 16 shows a diagram of example plots of sensor characteristics with varying sensing material (e.g., conductive fabric) elasticity (e.g., from relatively stiff to elastic), in accordance with example embodiments of the disclosure. In particular, diagram 1601 shows a unitless diagram of the trend for the output (e.g., output measurement) of the sensor versus the input (e.g., input force) for a given measurement quantity (e.g., force). Further, the plot of diagram 1601 indicates that for different inputs 1 and 2 corresponding to stiff and elastic, respectively, the output of the sensor may have a similar sensitivity (e.g., represented by the slope of the lines diagrams 1601), while having a different dynamic range (e.g., greater dynamic range for the elastic material as compared with the stiff material). Diagram 1603 shows the general trends for the output (e.g., output measurement of the sensor (in units of percent) versus time (e.g., in a given unit of time such as milliseconds, depending on the exact geometry and materials of the sensor). Further, the plot diagram 1603 shows that for different inputs 1 and 2 corresponding to increasing sensing material elasticity from stiff to elastic, respectively, the output of the sensor may take a shorter time to reach its final value absent transients (e.g., value corresponding to 100% on the output y-axis) for the stiffer sensing materials in the device sensors than for more elastic sensing materials.

Figure 17:
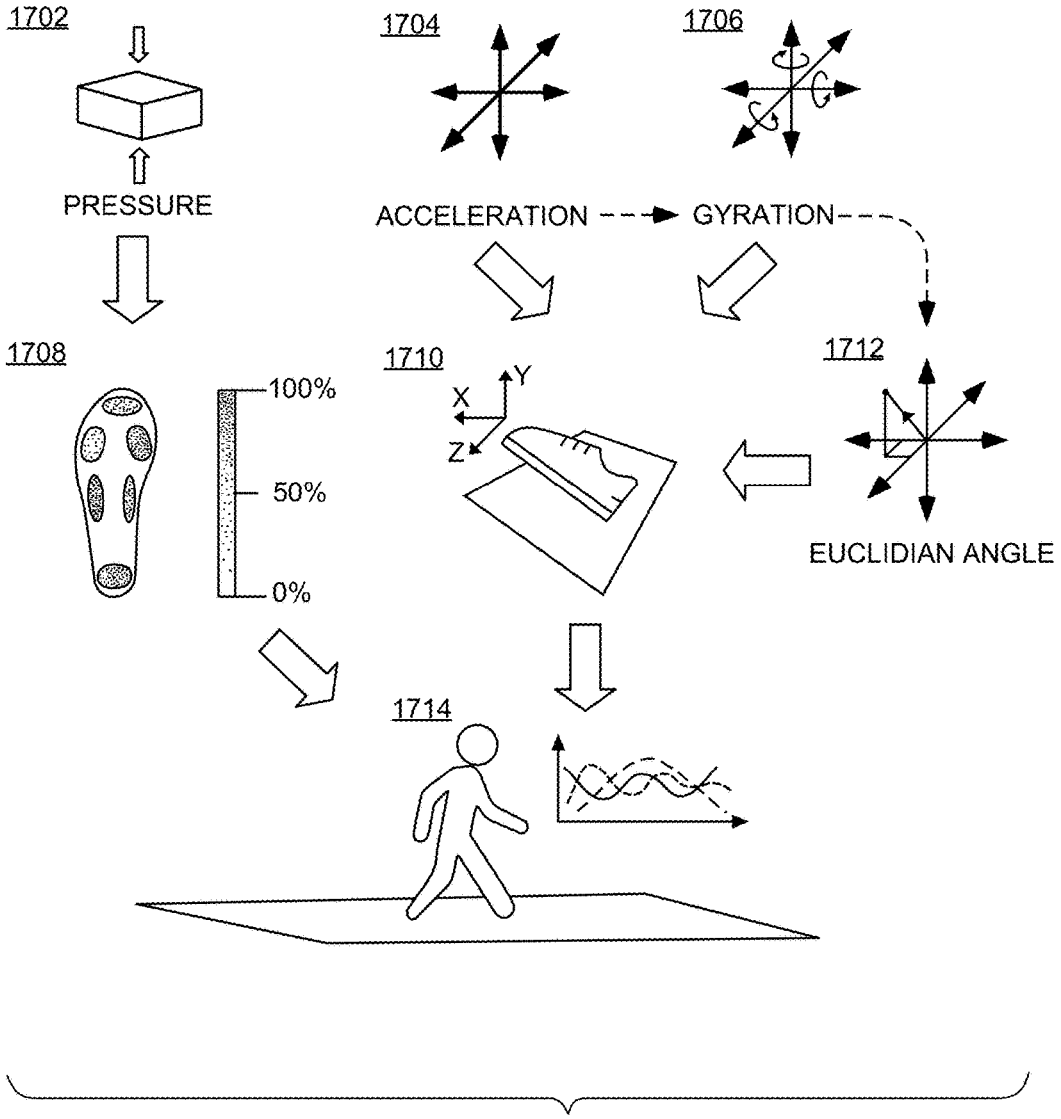
FIG. 17 shows example diagrams of example sensing mechanisms of the electronic devices described herein, in accordance with example embodiments of the disclosure.

FIG. 17 shows example diagrams of example sensing mechanisms of the electronic devices described herein, in accordance with example embodiments of the disclosure. In particular, diagram 1702 shows an example pressure sensing mechanism. In one embodiment, diagram 1704 shows an example acceleration ($m/s^2$) sensing mechanism. In another embodiment, diagram 1706 shows a gyration measurements (degrees/s) sensing mechanism. In another embodiment, diagram 1712 indicates that the acceleration and gyration measurements of the previous diagrams may be used to determine Euclidean angle by any suitable algorithm, for example, using an altitude and heading reference (AHRS) algorithm, including, but not limited to, a MahonyAHRS and/or a MadgwickAHRS algorithm. In one embodiment, diagram 1708 shows how pressure data can be visualized on an in-sole graphical heatmap. Alternatively, or additionally, data can be monitored numerically, for example, at a user device (e.g., a mobile phone) and at the user's discretion. In various embodiments, diagram 1714 shows a combination of acceleration, gyration, and Euclidean angle measurements as described above may be used to model the speed and/or orientation of the sole of a user in real-time or in near real-time.

In various embodiments, diagrams represent example techniques that may be used to acquire real-time gait and motion analysis using the wearable electronic devices described herein. In particular, a first set of sensors may be positioned strategically proximate to a given area of the body (e.g., the foot), and the set of sensors may be used to determine the motion of the given area body of the body (e.g., the foot, head, arm, etc.). In various embodiments, accelerometers and gyrometers may be used to capture motion in the form of 3-dimensional spatial data. In one embodiment, another second set of sensors (e.g., pressure, bend, and stretch sensors) may be arranged proximate to the given area of the body such that the sensors provide a 2-dimensional representation of movement and weight distribution of the body part on the sensors. Combined, these two sets of sensors may be used to determine the motion and movement patterns of the given area of the body. For example, the two sets of sensors may be used to determine the motion and/or gait patterns of a given user.

In various aspects, embodiments of the disclosure may be used to determine usage patterns of wearable electronic devices (e.g., electronic devices having pressure sensors). In one embodiment, electronic devices may include pressure sensitive materials (e.g., pressure sensitive fabrics), and wearable electronic devices may be used to sense intensity of a given motion by a given user. For example, for a first application, an electronic device may include a matrix of pressure sensitive pads in the shoe or sock to detect various parameters of a user's motion, including, but not limited to, foot placement, areas of impact, weight distribution, and time of impact and lift-off during a gait cycle, combinations thereof, and/or the like. In another example, a second application involving user's hands, an electronic device may be used, for example, to detect one or more of a grip strength, a finger/hand placement, pressure distribution among finger digits, combinations thereof, and/or the like. In further examples, an electronic device may be placed in the lining of clothing of a user may be used to detect level of fit, for example, whether a given article of clothing is too tight or too loose against the body of a user. In further embodiments, the electronic device may include one or more pressure sensors that may be positioned in a given article of clothing to detect deformation, body contortion, an amount of bend and flexibility, combinations thereof, and/or the like.

In various embodiments, one or more inertial measurement units (IMUs) may be used in connection with the disclosed electronic devices. In one embodiment, IMUs may include devices that may measure forces applied to the body, including, but not limited to, accelerative forces, angular forces, magnetic forces, barometric forces, combinations thereof, and/or the like. In particular, IMUs may include accelerometers and gyrometers to capture the acceleration and gyration of a moving body, for example, the rate of change in speed and angle of a body in motion. Further, each measurement of such sensors may be provided with reference to a 3-axis coordinate system (e.g., x, y, and z), with each axis providing a degree of freedom (DOF) for movement to be measured. In various embodiments, by combining both acceleration and gyration measurements, the IMU may provide a 6 DOF measurement. Such a measurement may be used by the electronic device to determine the Euler angles of a given body, thereby computing the orientation of the body in space at a particular time.

Figure 18:
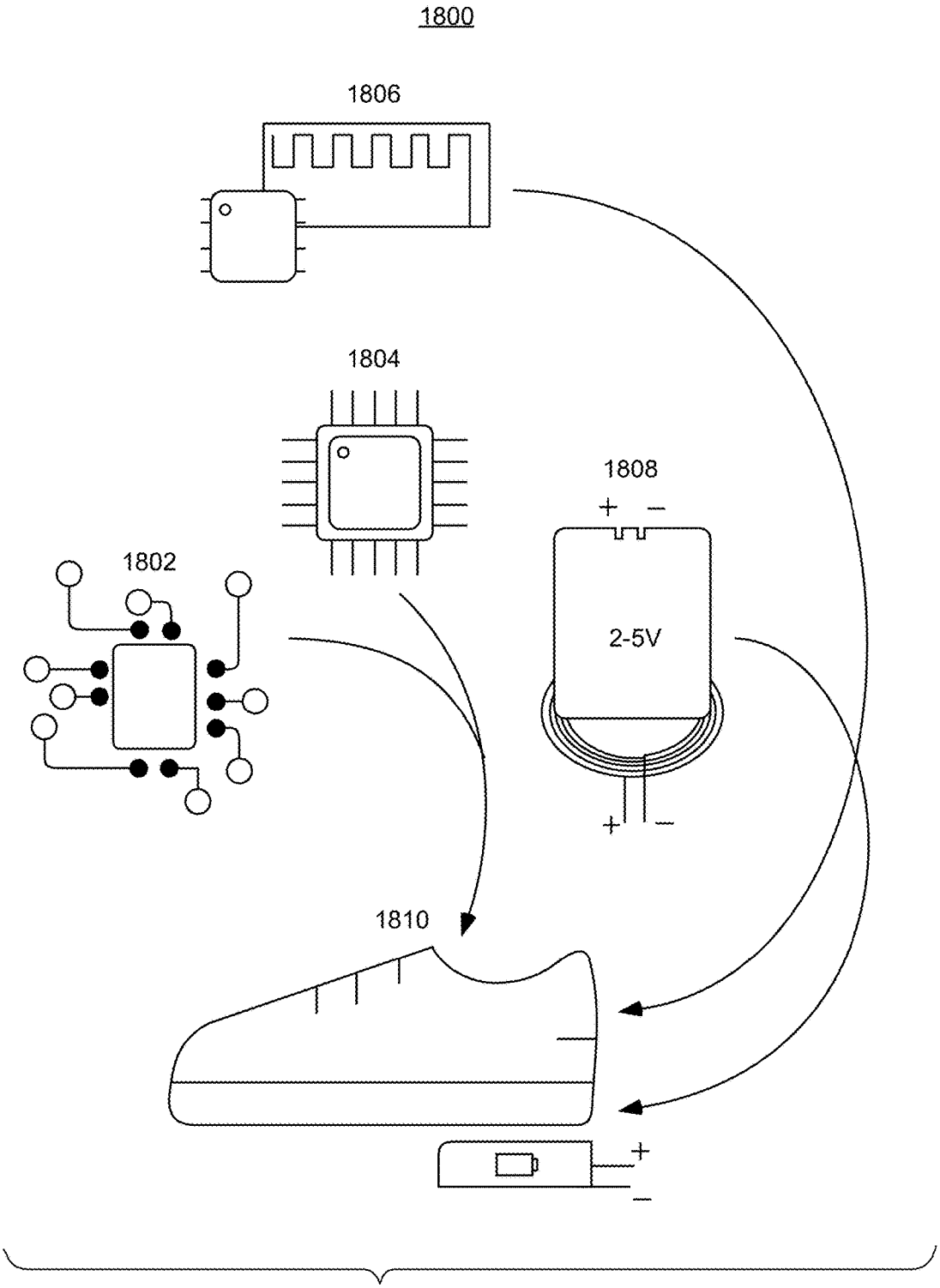
FIG. 18 shows an example diagram of an article of clothing including various components described herein, in accordance with example embodiments of the disclosure.

FIG. 18 shows an example diagram 1800 of an article of clothing including various components described herein, in accordance with example embodiments of the disclosure. In various embodiments, the components may include, but not be limited to, sensors, signal processing devices, logic devices, peripheral device controls, and the like. The component may be contained in a custom board and placed in a portion of the article of clothing such as in the tongue of the shoe, or anywhere that is comfortable for the user. In particular, diagram 1800 shows a shoe that may include at least three components: a microcontroller device 1804, a radio frequency (RF) device 1806, and a battery device 1808. In one aspect, the RF device may include a device configured to transmit and receive information based on a wireless connection (e.g., WiFi, Bluetooth, cellular, etc.) and may be placed in the back of the shoe, or anywhere that is comfortable for the user yet still externally accessible. In one embodiment, the battery device may include a battery pack that may be rechargeable through inductive charging, and the battery device may be placed at the base or sole of the shoe. In another embodiment, the components may be strategically placed in the shoe to maximize utilization and minimize user discomfort.

Hardware architecture & design considerations are described as follows. In particular, a circuitry with respects to shoe architecture may be an example design. In particular, hardware devices may include the microcontroller 1804. The hardware architecture consists of a centralized microcontroller that reads data from peripheral sensors such as the pressure and IMU devices 1802. Once the data is read, processed, and formatted into readable and usable data, the data is then transmitted via a radio frequency (RF) device 1806 to a specified receiver such as a server or personal computer in order to store and further process aggregated amounts of user data. In order to power this system, a rechargeable battery 1808 should provide enough voltage and current to provide enough power to sustain the system for hours at a time. Finally, these components can be strategically fitted into the shoe 1810, where the larger items such as the battery can be embedded into the sole-heel where it is easily accessible through inductive charging, and the microcontroller and remaining circuity can be distributed to the tongue or back of the shoe.

Figure 19:
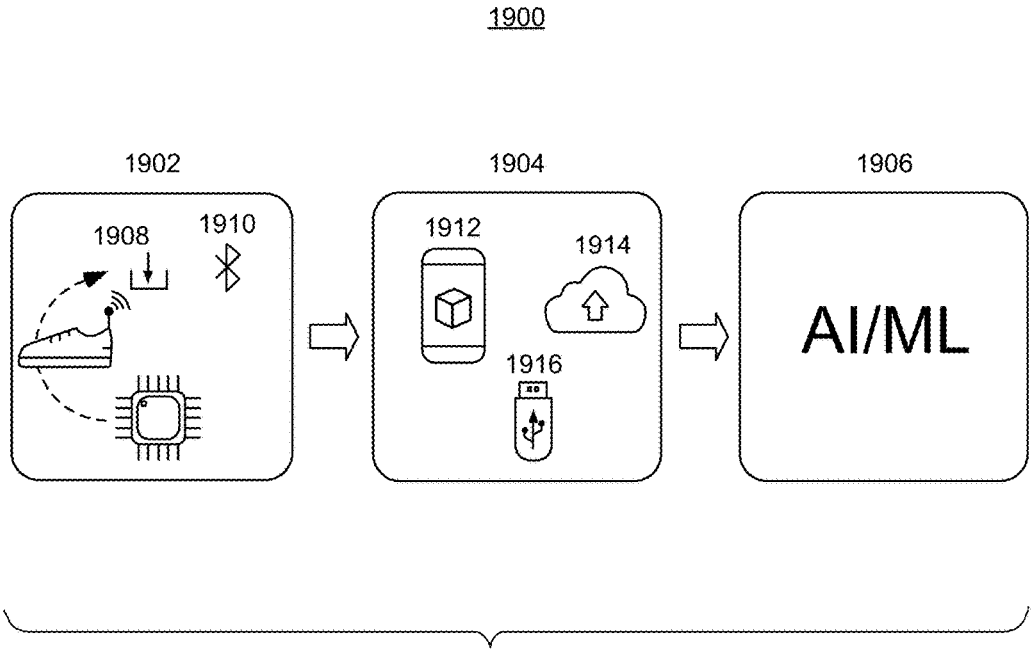
FIG. 19 shows a diagram representing an example flow of communication and data between the disclosed electronic devices and one or more peripheral devices, in accordance with example embodiments of the disclosure.

FIG. 19 shows a diagram 1900 representing an example flow of communication and data between the disclosed electronic devices and one or more peripheral device, in accordance with example embodiments of the disclosure. In various embodiments, data can be offloaded from an electronic device by wired or wireless connections 1902. In one embodiment, wired connections (e.g., USB) may be used to download the data to another computer or application for offline processing 1908. In another embodiment, a wireless connection 1910 may use any suitable air interface (e.g., WiFi, Bluetooth, etc.) to transfer data to another device such as an online server or application for data processing. In various embodiments, the offloaded data can be stored, analyzed, and shared using multiple online and offline methods 1904. In another embodiment, the data can be transferred to an app on the user's phone 1912. Alternatively, or additionally, the data can be uploaded and transferred via USB 1916. In further aspects, the data may be stored in the cloud 1914. Moreover, the data can be managed and analyzed using a server 1906 running one or more artificial intelligence (AI)-based algorithms to monitor data from an article of clothing having the electronic device(s), such as a shoe.

In various embodiments, the communication stack is described. In various embodiments, data collected by the electronic devices from the environment may be converted to electrical signals from the sensors of the electronic devices. Such data may then be transmitted to a microcontroller where it is processed into meaningful mathematical quantities. In one embodiment, the data may be sent to a written hard disk, or may be wirelessly transmitted to a local or personal server for further data aggregation and analysis. In particular, large data sets (e.g., high dimensional data sets) may be systematically generated by the sensors but may be computationally difficult to model with definitive mathematical functions that describe a state associated with the data (e.g., a walking or jumping state associated with sensor data). Accordingly, such large data sets may be used in connection with one or more machine learning applications where iterative reinforced learning algorithms can supply latent variables that are helpful in forming a predictive model describing the data. In one embodiment, machine learning algorithms may be used to design an AI system that learns from a user's motion and recognizes patterns or changes in the user's movement or gait. The AI algorithm may be used for tracking a user's performance, whether for athletic purposes like in sports training, or for tracking regular routines such as bending or stretching.

As discussed, the devices may be configured to run one or more AI-based algorithms. Such artificial intelligence (AI) to facilitate automating one or more features described herein. The components can employ various AI-based schemes for carrying out various embodiments and/or examples disclosed herein. To provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system, environment, etc. from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether the events are correlated in close temporal proximity, and whether the events and data come from one or several event and data sources (e.g., different sensor inputs). Components disclosed herein can employ various classification (explicitly trained (e.g., via training data) as well as implicitly trained (e.g., via observing behavior, preferences, historical information, receiving extrinsic information, etc.) schemes and/or systems (e.g., support vector machines, neural networks, expert systems, Bayesian belief networks, fuzzy logic, data fusion engines, etc.) in connection with performing automatic and/or determined action in connection with the claimed subject matter. Thus, classification schemes and/or systems can be used to automatically learn and perform a number of functions, actions, and/or determinations.

A classifier can map an input attribute vector, $z=(z_1, z_2, z_3, z_4, \ldots, z_n)$, to a confidence that the input belongs to a class, as by f(z)=confidence(class). Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, for example, naïve Bayes, Bayesian networks, decision trees, neural networks, fuzzy logic models, and/or probabilistic classification models providing different patterns of independence can be employed. Classification as used herein also is inclusive of statistical regression that is utilized to develop models of priority.

Figure 20:
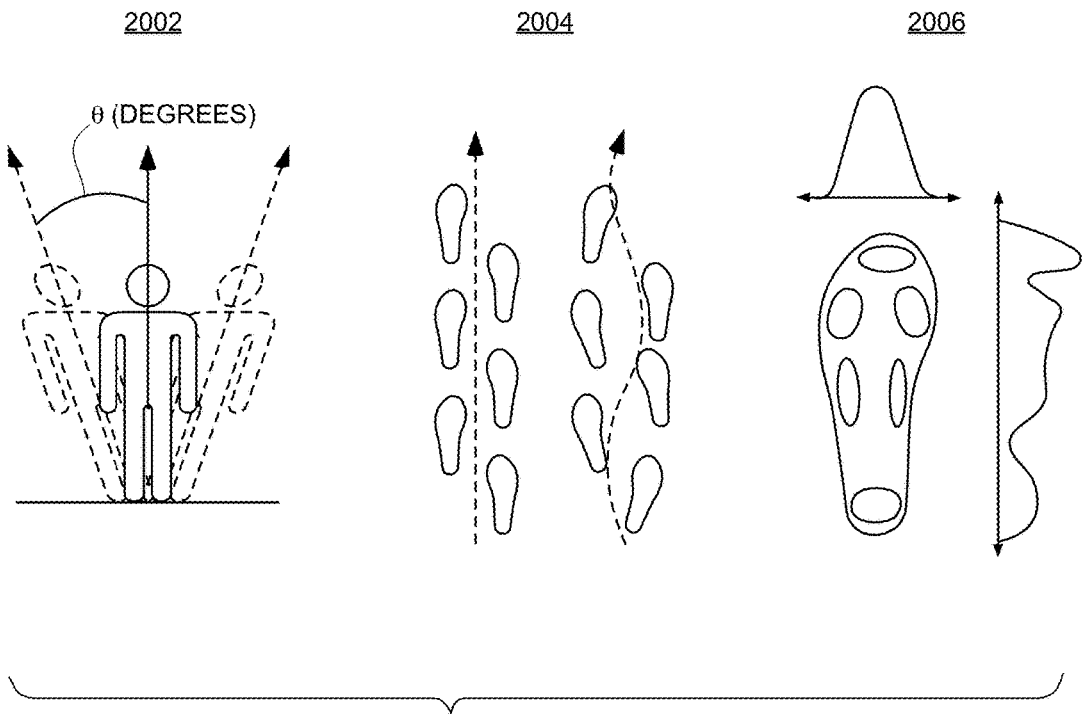
FIG. 20 shows diagrams of example applications for the disclosed electronic devices, in accordance with example embodiments of the disclosure.

FIG. 20 shows diagrams of example applications for the disclosed electronic devices, in accordance with example embodiments of the disclosure. In particular, FIG. 20 shows example applications for pressure and IMU sensing shoe technology. Diagram 2002 shows an example where the electronic devices may be used to determine the degree of tilt in a user's posture when idle or in motion. In particular, the degree of tilt may be indicative of degraded neurological activity of muscle control which manifest in poor balance. Diagram 2004 shows an example where the electronic devices may be used to determine a user's stepping gait, which can also reveal a degree of imbalance, poor muscle control, and overall degraded neurological control. On a more granular level, diagram 2006 shows an example where the electronic devices may be used to determine the weight distribution on a foot. This weight distribution may be used to determine signs of poor balance and muscle control, and when compared to healthy patients can provide detailed information about the user's level of neurological and bodily control.

As noted, embodiments of the disclosure may be used in connection with one or more machine learning and AI algorithms. In particular, a given user may have a unique range of motion and gait which can be attributed to one or more factors including, but not limited to, age, level of exercise, diet, and a variety of other physiological and external factors. In one embodiment, by determining quantifiable and high fidelity motion data using the disclosed electronic devices, a reverse analysis of a given user may be performed, that is, by knowing a user's motion data and gait performance, a trained professional or AI platform may be used to estimate the level of health or athletic condition of the user. For example, an Olympic athlete may have a different running style, posture, and range of motion, and the like than an average user. Such a distinction may be more apparent when comparing trained athletes to overweight or out-of-shape users. Such distinctions may be qualitatively measured through high-resolution videos and motion-captured images where they are meticulously analyzed by trained physical therapist and sports analyst. However, using the disclosed electronic devices, human motion can be captured in real time or near-real time and at higher quality without the use of expensive high-speed cameras and engineered rooms. Further, by using one or more AI-based algorithms, the human motions may be used in addition to or in place of subjective professional observations to increase the accuracy of analyses.

In various aspects, embodiments of the disclosure may be used in connection with healthcare sciences. In particular, neurological diseases may include one or more physical symptoms correlated to neurological degradation. For example, users suffering from Alzheimer's disease, Parkinson's disease, Huntington's disease, and the like may manifest poor physical outcomes such as debilitated walking, weakness, imbalance, and shakiness. Such physical symptoms may be difficult to detect at the onset, that is, during the beginnings of neurological damage; however, the symptoms may become severe and noticeable at later stages. Accordingly, conventional diagnostics of neurological diseases may rely on high-end and expensive measurements such as CT, MRI, or physical probing using EMG, EEG, and NCV scans. Moreover, physical assessment, even by trained professionals, may be subjective, inconsistent, and/or error-prone.

In various aspects, embodiments of the disclosure may offer the ability to detect the onset of neurological disorders by analyzing one or more changes in motion and gait patterns. For example, by tracking the daily motion and/or the walking patterns of the user, and analyzing this data using one or more AI-based algorithms that are configured to detect cues associated with motion impairment, embodiments of the disclosure may be used to predict the onset of neurological disorders and provide feedback to the user. Thereby, rather than seeing a doctor at discrete points in time, a patient can go on with their normal routine, as walking and moving may provide sufficient data to the AI-based algorithms to discern changes in physical function. Further, noticeable changes may be analyzed by the AI-based algorithms and communicated to the user and/or doctors for more thorough analysis.

In various aspects, embodiments of the disclosure may be used in connection with athletics application. In particular, athletic fields are using more devices that may serve to aid in providing athletic assessment, feedback, and quantitative measurements of performance to users. Many athletic devices are peripheral as they are added to areas that are most comfortable rather than more functional. Examples of such athletic devices include smart watches, phones, and belt/clothing clip-ons. Some of these device may be unable to perform on-site data collection. For example, for phones and smart watches, counting steps may require multiple devices and sophisticated algorithms to indirectly monitor foot motions. In contrast, the disclosed electronic devices may already be placed in a given article of clothing such as a shoe, and thereby, making certain measurements such as step counts may performed in a more straightforward fashion. Accordingly, creating wearable electronics in the shoe that are comfortable opens a new arena of accurate and direct measurement of one or more gait, speed, step count, running style combinations thereof, and/or the like, which may not be easily and/or directly measured with a phone or watch located at a distance (e.g., a body's length) way from the measurement site (e.g., a foot of a user).

Figure 21:
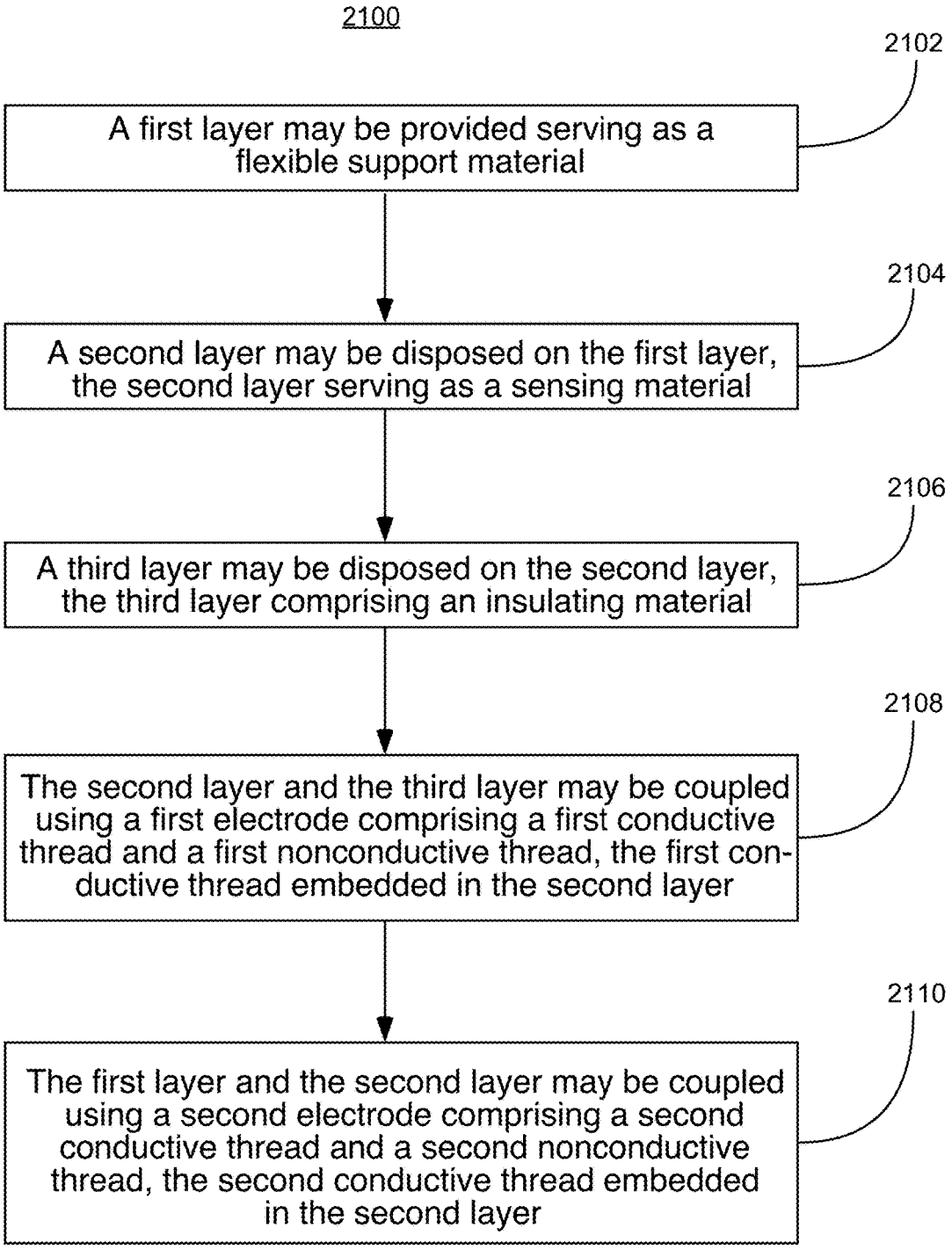
FIG. 21 shows an example flow diagram that may represent aspects of the fabrication of the electronic devices described herein, in accordance with example embodiments of the disclosure.

FIG. 21 shows an example flow diagram 2100 that may represent aspects of the fabrication of the electronic devices described herein, in accordance with example embodiments of the disclosure. At block 2102, a first layer may be provided serving as a flexible support material. At block 2104, a second layer may be disposed on the first layer, the second layer serving as a sensing material. At block 2106, a third layer may be disposed on the second layer, the third layer comprising an insulating material. At block 2108, the second layer and the third layer may be coupled using a first electrode comprising a first conductive thread and a first non-conductive thread, the first conductive thread embedded in the second layer. At block 2110, the first layer and the second layer may be coupled using a second electrode comprising a second conductive thread and a second non-conductive thread, the second conductive thread embedded in the second layer.

In another embodiment, a fourth layer may be disposed on the first layer, the fourth layer serving as a second sensing material. In one embodiment, the third layer may be disposed on the fourth layer, the third layer comprising the insulating material. In another embodiment, the fourth layer and the third layer may be coupled using a third electrode comprising a third conductive thread and a third non-conductive thread, the third conductive thread embedded in the fourth layer. In one embodiment, the fourth layer and the first layer may be coupled using a fourth electrode comprising a fourth conductive thread, the fourth conductive thread embedded in the first layer and the fourth layer. Further, a cross-sectional shape of the electrodes and/or a spacing between two or more electrodes may be performed to increase a response time, an input dynamic range, an output dynamic range, and/or a sensitivity of the sensor. In some embodiments, the sensor is a first sensor, and the method further includes fabricating a second sensor spaced laterally from the first sensor along a common horizontal axis or a common vertical axis.

In various embodiments, electrospinning/spraying and spray painting may be used to fabricate the devices described herein. In particular, such techniques may aerosolizes conductive materials (metals or conductive polymers) and embed them into a porous medium (in this case, a fabric or thread) through electrostatic interactions (applying a voltage, charging the fabric/thread and the aerosolized material with the opposite charge). Alternatively, or additionally, screen printing may be performed to generate the devices described herein. In particular, air pressure (spray painting), or force applied to a liquid slurry of the aerosolized conductive materials in order to paint the materials on the fabric may be used to create at least portions of the devices described herein.

Another approach in fabrication may include using electrospinning/spraying or spray painting to spray on the electrodes. Connections can be joined using the sewing technique already specified in this disclosure.

As mentioned, one or more databases used in connection with the disclosure can include a database stored or hosted on a cloud computing platform. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware based systems that perform the specified functions or acts or carry out combinations of special purpose hardware and computer instructions.

Figure 22:
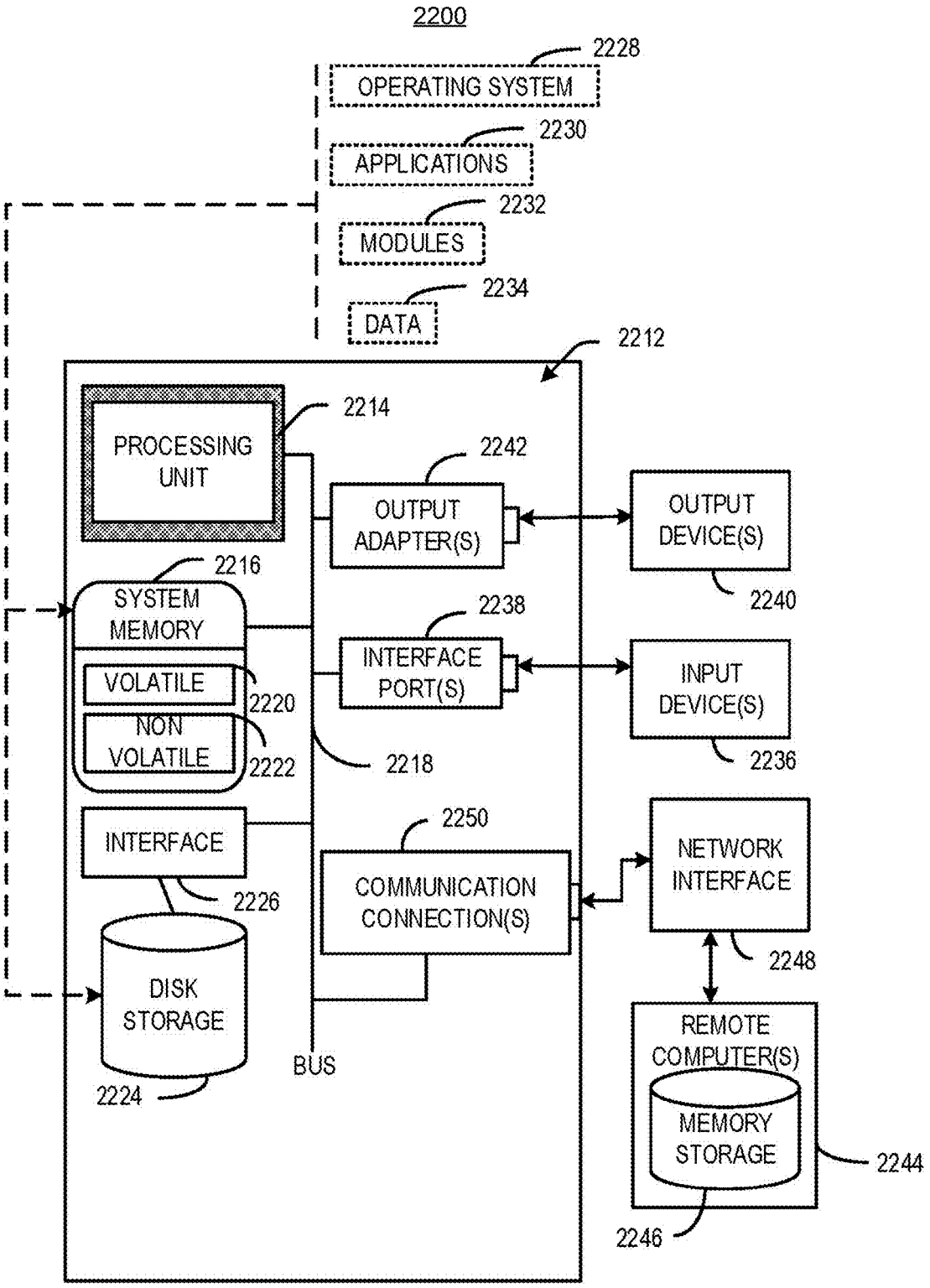
FIG. 22 shows a diagram of an example computational environment for the electronic devices described herein, in accordance with example embodiments of the disclosure.

In order to provide a context for the various aspects of the disclosed subject matter, FIG. 22 as well as the following discussion are intended to provide a general description of a suitable environment in which the various aspects of the disclosed subject matter can be implemented. FIG. 22 illustrates a block diagram of an example, non-limiting operating environment 2200 in which one or more embodiments described herein can be facilitated. Repetitive description of like elements employed in other embodiments described herein is omitted for sake of brevity. With reference to FIG. 22, a suitable operating environment 2200 for implementing various aspects of this disclosure can include a computer 2212. The computer 2212 can also include a processing unit 2214, a system memory 2216, and a system bus 2218. The system bus 2218 can operably couple system components including, but not limited to, the system memory 2216 to the processing unit 2214. The processing unit 2214 can be any of various available processors. Dual microprocessors and other multiprocessor architectures also can be employed as the processing unit 2214. The system bus 2218 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 2216 can also include volatile memory 2220 and nonvolatile memory 2222. The basic input/output system (BIOS), containing the basic routines to transfer information between elements within the computer 2212, such as during start-up, can be stored in nonvolatile memory 2222. By way of illustration, and not limitation, nonvolatile memory 2222 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 2220 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 2212 can also include removable/non-removable, volatile/non-volatile computer storage media. FIG. 22 illustrates, for example, a disk storage 2224. Disk storage 2224 can also include, but is not limited to, devices like a magnetic disk drive, floppy disk drive, tape drive, Jaz drive, Zip drive, LS-100 drive, flash memory card, or memory stick. The disk storage 2224 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 2224 to the system bus 2218, a removable or non-removable interface can be used, such as interface 2226. FIG. 22 also depicts software that can act as an intermediary between users and the basic computer resources described in the suitable operating environment 2200. Such software can also include, for example, an operating system 2228. Operating system 2228, which can be stored on disk storage 2224, acts to control and allocate resources of the computer 2212. System applications 2230 can take advantage of the management of resources by operating system 2228 through program components 2232 and program data 2234, e.g., stored either in system memory 2216 or on disk storage 2224. It is to be appreciated that this disclosure can be implemented with various operating systems or combinations of operating systems. A user enters commands or information into the computer 2212 through one or more input devices 2236. Input devices 2236 can include, but are not limited to, a pointing device such as a mouse, trackball, stylus, touch pad, keyboard, microphone, joystick, game pad, satellite dish, scanner, TV tuner card, digital camera, digital video camera, web camera, sensors mentioned above, and the like. These and other input devices can connect to the processing unit 2214 through the system bus 2218 via one or more interface ports 2238. The one or more Interface ports 2238 can include, for example, a serial port, a parallel port, a game port, and a universal serial bus (USB). One or more output devices 2240 can use some of the same type of ports as input device 2236. Thus, for example, a USB port can be used to provide input to computer 2212, and to output information from computer 2212 to an output device 2240. Output adapter 2242 can be provided to illustrate that there are some output devices 2240 like monitors, speakers, and printers, among other output devices 2240, which require special adapters. The output adapters 2242 can include, by way of illustration and not limitation, video and sound cards that provide a means of connection between the output device 2240 and the system bus 2218. It should be noted that other devices and/or systems of devices provide both input and output capabilities such as one or more remote computers 2244.

Computer 2212 can operate in a networked environment using logical connections to one or more remote computers, such as remote computer 2244. The remote computer 2244 can be a computer, a server, a router, a network PC, a workstation, a microprocessor based appliance, a peer device or other common network node and the like, and typically can also include many or all of the elements described relative to computer 2212. For purposes of brevity, only a memory storage device 2246 is illustrated with remote computer 2244. Remote computer 2244 can be logically connected to computer 2212 through a network interface 2248 and then physically connected via communication connection 2250. Further, operation can be distributed across multiple (local and remote) systems. Network interface 2248 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 2250 refers to the hardware/software employed to connect the network interface 2248 to the system bus 2218. While communication connection 2250 is shown for illustrative clarity inside computer 2212, it can also be external to computer 2212. The hardware/software for connection to the network interface 2248 can also include, for exemplary purposes only, internal and external technologies such as, modems including regular telephone grade modems, cable modems and DSL modems, ISDN adapters, and Ethernet cards.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram or blocks.

While the subject matter has been described above in the general context of computer-executable instructions of a computer program product that runs on a computer and/or computers, those skilled in the art will recognize that this disclosure also can or can be implemented in combination with other program modules or components. Generally, program modules or components include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules or components can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAIVI), Synchlink DRAM (SLDRAM), direct Rambus RAM (DRRAM), direct Rambus dynamic RAM (DRDRAIVI), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device [comprising at least one sensor, the sensor] comprising:

a first sensor, comprising:

a first layer serving as a flexible support material;

a second layer on the first layer, the second layer serving as a sensing material; and a third layer on the second layer, the third layer comprising an insulating material, wherein the second layer and the third layer are coupled using a first electrode comprising a first conductive thread and a first non-conductive thread, the first conductive thread embedded in the second layer, and wherein the first layer and the second layer are further coupled using a second electrode comprising a second conductive thread and a second non-conductive thread, the second conductive thread embedded in the second layer, and a second sensor spaced laterally from the first sensor along a common horizontal axis or a common vertical axis, the second sensor comprising:

the first layer serving as the flexible support material for the second sensor;

a fourth layer on the first layer, the fourth layer serving as a second sensing material; and the third layer on the fourth layer, the third layer comprising the insulating material, wherein the fourth layer and the third layer are coupled using a third electrode comprising a third conductive thread and a third non-conductive thread, the third conductive thread embedded in the fourth layer, and wherein the fourth layer and the first layer are coupled using a fourth electrode comprising a fourth conductive thread, the fourth conductive thread embedded in the first layer and the fourth layer.

2. The device of claim [1] *30*, wherein [a material composition for] at least one of the flexible support material, the sensing material, and the insulating material [is selected from the group consisting of] *comprises* a fabric [and] *or* a polymer.

3. The device of claim [1] *30*, wherein the sensing material comprises a dopant, wherein the dopant is selected from [the group consisting] *one or more* of a group I element, a group II element, a transition metal, a group III element, a group IV element, a group V element, a group VI element, *and* a group VII element[, and combinations thereof].

4. The device of claim [1] *30*, wherein a composition of at least one of the first conductive thread[,] *or* the second conductive thread[, the third conductive thread, and the fourth conductive thread] is selected from [the group consisting] *one or more* of a metal and a conductive polymer.

5. The device of claim [1] *30*, wherein a density per unit area of a stitching of at least one of the first conductive thread[,] *or* the second conductive thread[, the third conductive thread, and the fourth conductive thread] is configured to alter *one or more of* a response time, an input dynamic range, an output dynamic range, [and/or] *and* a sensitivity of the sensor.

6. The device of claim [1] *30*, wherein a radius of at least one of the first conductive thread[,] *or* the second conductive thread[, the third conductive thread, and the fourth conductive thread] is configured to alter one or more of a response time, an input dynamic range, an output dynamic range, [and/or] *and* a sensitivity of the sensor.

7. The device of claim [1] *30*, wherein a thickness of the sensing material is between about 100 nanometers and about 1 centimeter, and wherein the thickness of the sensing material is configured to alter *one or more of* a response time, an input dynamic range, an output dynamic range, [and/or] *and* a sensitivity of the sensor.

8. The device of claim [1] *30*, wherein (i) a cross-sectional shape of the first electrode[,] *or* the second electrode[, the third electrode, and the fourth electrode,] or (ii) a spacing between [two or more of] the first electrode[,] *and* the second electrode[, the third electrode, and the fourth electrode,]; *or* (*iii*) *a thickness of the sensing material* is configured to alter *one or more of* a response time, an input dynamic range, an output dynamic range, [and/or] *and* a sensitivity of the sensor.

9. An article [comprising] *having* at least one device, the device comprising:

a first sensor comprising:

a first sensing material and a first electrode along a top edge of the first sensing material, the first sensing material *being* wired to a first signal output, and a second electrode along a bottom edge of the first sensing material, the second electrode coupled to a first insulating material[;], *wherein at least one of the first electrode or the second electrode comprises a conductive thread sewn into at least one of the first sensing material or the first insulating material.*

[a second sensor spaced vertically from the first sensor across the first insulating material, the second sensor comprising:

a second sensing material and a third electrode electrically connected to the second electrode, the second sensing material wired to a common electrical connection, the third electrode passing from a top edge of the second sensing material to a bottom edge of the second sensing material, the third electrode coupled to a second insulating material, and a fourth electrode along a top edge of the second sensing material, the fourth electrode wired to a second signal output; and a third sensor spaced vertically from the second sensor across the second insulating material, the third sensor comprising:

a third sensing material, a fifth electrode along a top edge of the third sensing material wired to the common electrical connection, and a sixth electrode along a bottom edge of the third sensing material, the sixth electrode wired to a third signal output.]

10. The article of claim [9] *28*, wherein the first insulating material is disposed on a top side of the article, and wherein the second insulating material is disposed on a bottom side of the article.

11. The article of claim 9, wherein [a material composition of] at least *one* of the first sensing material, [the second sensing material, the third sensing material,] *or* the first insulating material[, and the second insulating material is selected from the group consisting of] *comprises* a fabric [and] *or* a polymer material.

12. The article of claim 9, wherein [at least one of] the first sensing material[, the second sensing material, and the third sensing material] comprises a dopant, wherein the dopant is selected from [the group consisting] *one or more* of a group I element, a group II element, a transition metal, a group III element, a group IV element, a group V element, a group VI element, a group VII element[, and combinations thereof].

13. The article of claim 9, wherein a thickness of [at least one of] the first sensing material[, the second sensing material, and the third sensing material] is between about 100 nanometers to about 1 centimeter, and wherein the thickness of the first sensing material[, the second sensing material, or the third sensing material] is configured to alter *one or more of* a response time, an input dynamic range, an output dynamic range, [and/or] *and* a sensitivity of the first sensor, the second sensor, or the third sensor.

14. The article of claim 9, wherein (i) a cross-sectional shape of the first electrode[,] *and* the second electrode[, the third electrode, the fourth electrode, the fifth electrode, and the sixth electrode] or (ii) a spacing between [two or more of] the first electrode[,] *and* the second electrode[, the third electrode, the fourth electrode, the fifth electrode, and the sixth electrode] is configured to alter *one or more of* a response time, an input dynamic range, an output dynamic range, [and/or] *and* a sensitivity of the first sensor, the second sensor, or the third sensor.

15. The article of claim [9] *29*, wherein a normal force acting on a portion of the first sensing material generates a compression of the first sensor and a tension on the third sensor.

16. The article of claim 15, wherein the first sensor, the second sensor, and the third sensor generate a bend signal, a pressure signal, and a stretch signal based on the compression and the tension.

*17. The device of claim 30, wherein the first sensor is configured to generate one or more of a bend signal, a pressure signal, a stretch signal, or a signal resulting from a physical deformation of the sensing material.*

*18. The device of claim 30, wherein one or more of the first conductive thread, the first non-conductive thread, and the second conductive thread is independently exposed on a surface of the first layer or the second layer.*

*19. The device claim 30, wherein one or more of the first conductive thread or the second conductive thread is patterned to comprise one or more exposed regions on the second layer, wherein lengths of the one or more exposed regions are configured to alter one or more of a response time, an input dynamic range, an output dynamic range, and a sensitivity of the sensor.*

*20. The device of claim 30, wherein at least one of resistivity, capacitance, or inductance of the sensing material is configured to correspond to an expected pressure load on the sensing material.*

*21. The device of claim 30 further comprising one or more additional sensors, wherein the first sensor and the one or more additional sensors have sensing orthogonality properties, and wherein signals received from the first sensor and the one or more additional sensors in response to a physical deformation of the sensing material have opposite signs.*

*22. The device of claim 30, wherein a degree of capacitance between the first electrode and the second electrode is configured to correspond to a measure of deformation of the flexible support material.*

*23. The device of claim 30, further comprising an array of sensors including the first sensor, the array of sensors being arranged on the flexible support material in a pattern configured to measure electric field tomography.*

*24. The device of claim 23, wherein the array of sensors comprises a first electrode pair and two or more neighboring electrodes,*

*wherein the first electrode pair is configured to emit one or more signals,*

*wherein the two or more neighboring electrodes are configured to measure voltage values at the two or more neighboring electrodes, and*

*wherein differences in the voltage values correspond to a location on the flexible support material where a force is applied.*

*25. The device of claim 30, further comprising an array of sensors including the first sensor, the array of sensors*

*being arranged on the flexible support material in a pattern configured to measure electric impedance tomography,*

*wherein one or more pairs of electrodes, including the first electrode and the second electrode, in the array of sensors are configured to measure values of resistance corresponding to locations of the one or more pairs of electrodes, and*

*wherein a change in the values of resistance corresponds to a location on the flexible support material where a deformation occurred.*

*26. The device of claim 30, further comprising:*

*an array of sensors including the first sensor, the array of sensors being arranged on different locations of the flexible material; and*

*a radio frequency (RF) transceiver configured to capture one or more RF signals from the array of sensors, wherein the one or more captured RF signals corresponds to positions of the array of sensors relative to the RF transceiver.*

*27. An article comprising the device of claim 1, wherein the article is at least one of a garment, a shoe, a sock, an insole, pants, a shirt, an undergarment, or a hat.*

*28. The article of claim 9, wherein the device further comprises:*

*a second sensor spaced vertically from the first sensor across the first insulating material, the second sensor comprising:*

*a second sensing material and a third electrode electrically connected to the second electrode, the second sensing material wired to a common electrical connection, the third electrode passing from a top edge of the second sensing material to a bottom edge of the second sensing material, the third electrode coupled to a second insulating material, and*

*a fourth electrode along a top edge of the second sensing material, the fourth electrode wired to a second signal output.*

*29. The article of claim 28, wherein the device further comprises:*

*a third sensor spaced vertically from the second sensor across the second insulating material, the third sensor comprising:*

*a third sensing material,*

*a fifth electrode along a top edge of the third sensing material wired to the common electrical connection, and*

*a sixth electrode along a bottom edge of the third sensing material, the sixth electrode wired to a third signal output.*

*30. A device comprising:*

*a second sensor spaced laterally from a first sensor along a common horizontal axis or a common vertical axis, the second sensor comprising:*

*a first layer serving as a flexible support material for the second sensor;*

*a second layer on the first layer, the second layer serving as a sensing material; and*

*a third layer on the second layer, the third layer comprising an insulating material,*

*wherein the second layer and the third layer are coupled using a first electrode comprising a first conductive thread and a first non-conductive thread, the first conductive thread being sewn into the second layer, and*

*wherein the second layer and the first layer are coupled using a second electrode comprising a second conductive thread, the second conductive thread being sewn into the first layer and the second layer.*

* * * * *